United States Patent [19]

Lemieux et al.

[11] 4,195,174

[45] Mar. 25, 1980

[54] SYNTHESIS OF 2-AMINO-2-DEOXYGLYCOSES AND 2-AMINO-2-DEOXYGLYCOSIDES FROM GLYCALS

[75] Inventors: Raymond U. Lemieux; R. Murray Ratcliffe, both of Edmonton, Canada

[73] Assignee: Chembiomed Ltd., Edmonton, Canada

[21] Appl. No.: 894,366

[22] Filed: Apr. 7, 1978

[30] Foreign Application Priority Data

Apr. 14, 1977 [GB] United Kingdom .............. 15536/77

[51] Int. Cl.$^2$ .......................................... C07H 11/02
[52] U.S. Cl. .................................... 536/18; 424/180; 536/4; 536/53; 536/115; 536/119; 536/122
[58] Field of Search ................. 536/4, 18, 53, 115, 536/122, 119

[56] References Cited

U.S. PATENT DOCUMENTS

| | | | |
|---|---|---|---|
| 2,039,046 | 4/1936 | Wyler | 536/18 |
| 2,094,693 | 10/1937 | Wyler | 536/18 |
| 2,105,389 | 1/1938 | Wyler | 536/18 |
| 3,496,196 | 2/1970 | Suami et al. | 536/18 |
| 3,681,398 | 8/1972 | Umezawa et al. | 536/18 |
| 3,935,184 | 1/1976 | Jones et al. | 536/53 |
| 3,953,422 | 4/1976 | Pfeiffer | 536/53 |
| 4,039,663 | 8/1977 | Areamone et al. | 536/122 |
| 4,064,339 | 12/1977 | Coussediere et al. | 536/122 |
| 4,105,760 | 8/1978 | Szejtli et al. | 536/122 |

*Primary Examiner*—Johnnie R. Brown
*Attorney, Agent, or Firm*—Ernest Peter Johnson

[57] ABSTRACT

O-acetylated glycals react with ceric ammonium nitrate in the presence of sodium azide to provide, in good yield, O-acetylated 2-azido-2-deoxy glycosyl nitrates. These nitrates can be used to prepare 2-amino-2-deoxy sugars, such as D-galactosamine and lactosamine. The O-acetylated 2-azido-2-deoxy glycosyl nitrates can alternately be converted to O-acetylated 2-azido-2-deoxy glycosyl halides which are useful in the preparation of O-acetylated 2-azido-2-deoxy glycosides, which in turn can be reduced to 2-amino-2-deoxy glycosides. Of particular interest are the syntheses of 2-amino-2-deoxy glycosides which correspond to the terminal units of the antigenic determinant for the human A blood group. Attachment of these glycosides to a solid support provides immunoabsorbents which efficiently and preferentially absorb anti-A antibodies from blood plasma.

22 Claims, 14 Drawing Figures

Fig. 1a.
FORMULA SHEET
I 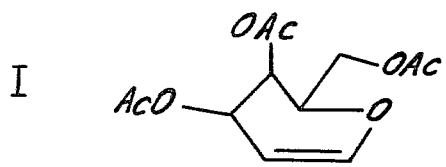 3,4,6-tri-O-acetyl-D-galactal
II 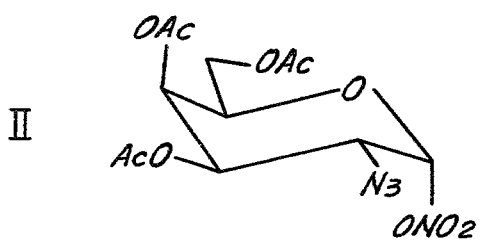 3,4,6-tri-O-acetyl-2-azido-2-deoxy-α-D-galactopyranosyl nitrate
III 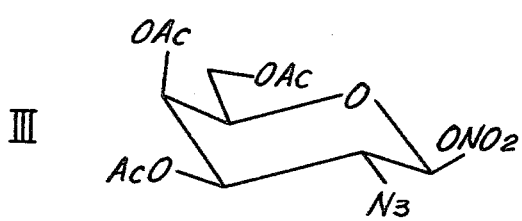 3,4,6-tri-O-acetyl-2-azido-2-deoxy-β-D-galactopyranosyl nitrate
IV 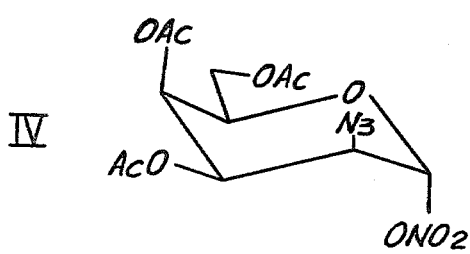 3,4,6-tri-O-acetyl-2-azido-2-deoxy-α-D-talapyranosyl nitrate
V 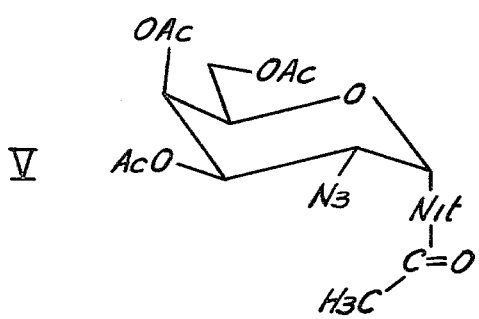 N-(3,4,6-tri-O-acety-2-azido-2-deoxy-α-D-galactopyranosyl) acetamide

Fig. 1b.
VI 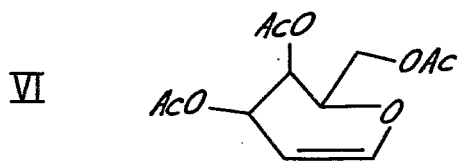 3,4,6-tri-_O_-acetetyl-_D_-glucal
VII 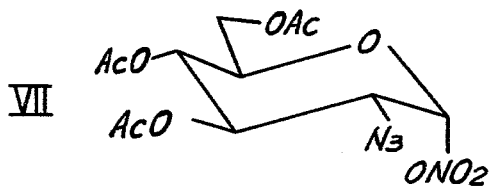 3,4,6-tri-_O_-acetetyl-2-azido-2-deoxy-α-_D_-glucopyranosyl nitrate
VIII 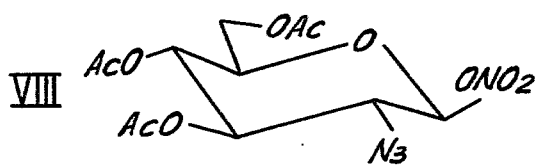 3,4,6-tri-_O_-acetetyl-2-azido-2-deoxy-β-_D_-glucopyranosyl nitrate
IX 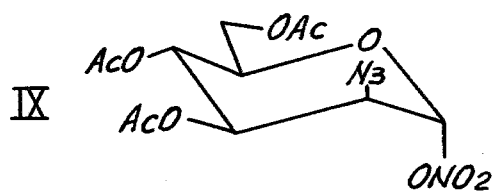 3,4,6-tri-_O_-acetyl-2-azido-2-deoxy-α-D-mannopyranosyl nitrate
X 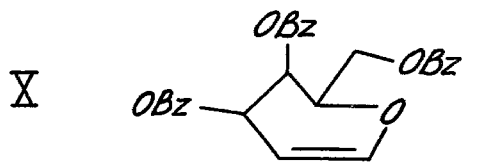 3,4,6-tri-_O_-benzoyl-_D_-galactal
XI 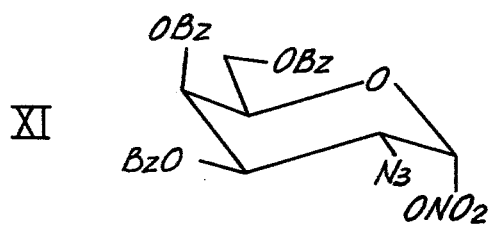 3,4,6-tri-_O_-benzoyl-2-azido-2-deoxy-α-_D_-galactopyranosyl nitrate
XII 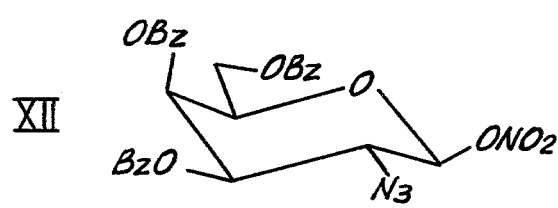 3,4,6-tri-_O_-benzoyl-2-azido-2-deoxy-β-_D_-galactopyranosyl nitrate

Fig. 1c.
XIII
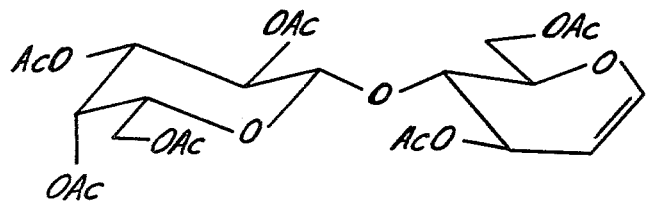
3,6,2',3',4',6'-hexa-O-acetyl-D-lactal
XIV
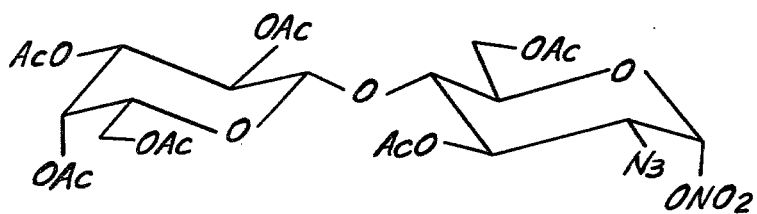
3,6-di-O-acetyl-4-O-(2,3,4,6-tetra-O-acetyl-β-D-galactopyranosyl)-2-azido-2-deoxy-α-D-glucopyranosyl nitrate
XV
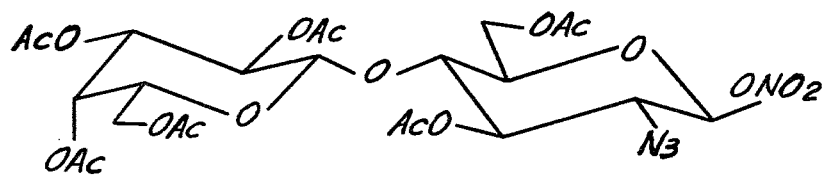
3,6-di-O-acetyl-4-O-(2,3,4,6-tetra-O-acetyl-β-D-galactopyranosyl)-2-azido-2-deoxy-β-D-glucopyranosyl nitrate
XVI
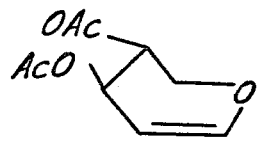
3,4-di-O-acetyl-D-xylal
XVII
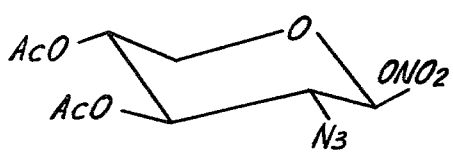
3,4-di-O-acetyl-2-azido-2-deoxy-β-D-xylopyranosyl nitrate
XVIII
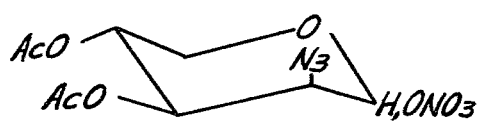
3,4-di-O-acetyl-2-azido-2-deoxy-α/β-D-lyxopyranosyl nitrate

Fig. 1d.
XIX 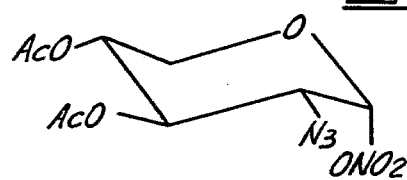 3,4-di-*O*-acetyl-2-azido-2-deoxy-α-_D_-xylopyranosyl nitrate
XX 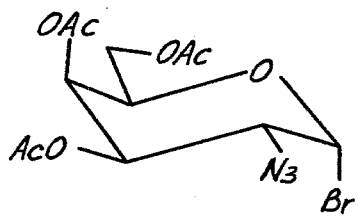 3,4,6-tri-*O*-acetyl-2-azido-2-deoxy-α-_D_-galactopyranosyl bromide
XXI 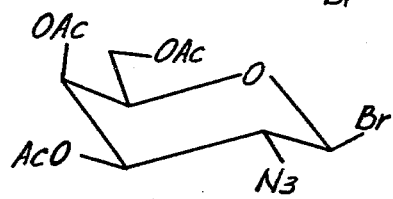 3,4,6-tri-*O*-acetyl-2-azido-2-deoxy-β-_D_-galactopyranosyl bromide
XXII 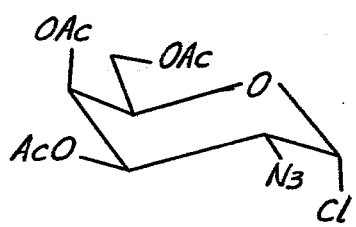 3,4,6-tri-*O*-acetyl-2-azido-2-deoxy-α-_D_-galactopyranosyl chloride
XXIII 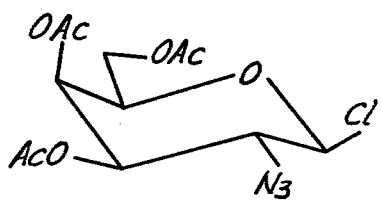 3,4,6-tri-*O*-acetyl-2-azido-2-deoxy-β-_D_-galactopyranosyl chloride
XXIV 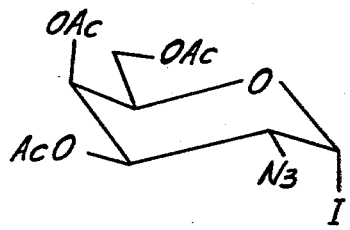 3,4,6-tri-*O*-acetyl-2-azido-2-deoxy-α-_D_-galactopyranosyl iodide

Fig. 1e.
XXV
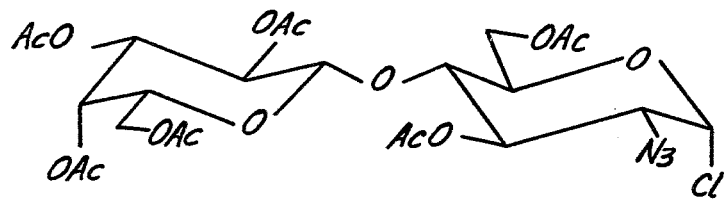
3,6-di-O-acetyl-4-O-(2,3,4,6-tetra-O-acetyl-β-D-galactopyranosyl)-2-azido-2-deoxy-α-D-glucopyranosyl chloride
XXVI
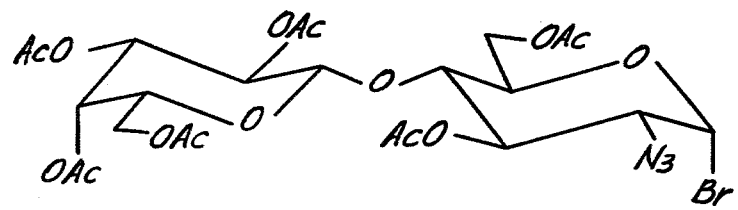
3,6-di-O-acetyl-4-O-(2,3,4,6-tetra-O-acetyl-β-D-galactopyranosyl)-2-azido-2-deoxy-α-D-glucopyranosyl bromide
XXVII
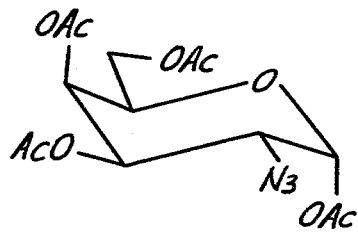
1,3,4,6-tetra-O-acetyl-2-azido-2-deoxy-α-D-galactopyranse
XXVIII
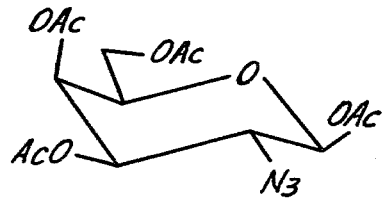
1,3,4,6-tetra-O-acetyl-2-azido-2-deoxy-β-D-galactopyranose
XXIX
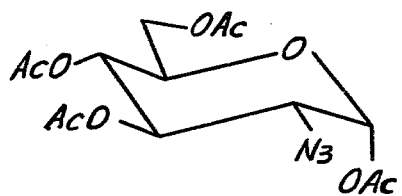
1,3,4,6-tetra-O-acetyl-2-azido-2-deoxy-α-D-glucopyranose

Fig. 1f.
XXX 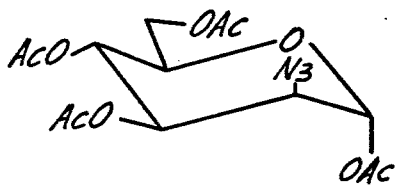
1,3,4,6-tetra-O-acetyl-2-azido-2-deoxy-α-D-mannopyranose
XXXI 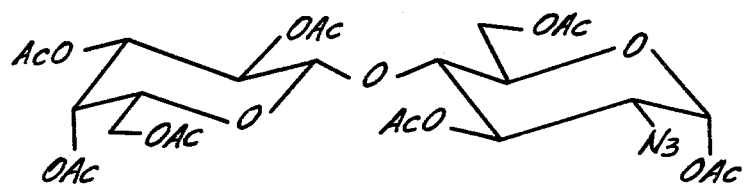
1,3,6-tri-O-acetyl-4-O-(2,3,4,6-tetra-O-acetyl-β-D-galactopyranosyl)-2-azido-2-deoxy-α-D-glucopyranose
XXXII 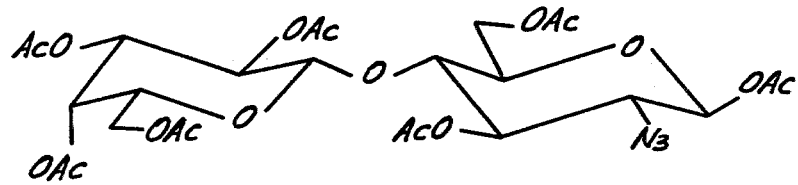
1,3,6-tri-O-acetyl-4-O-(2,3,4,6-tetra-O-acetyl-β-D-galactopyranosyl)-2-azido-2-deoxy-β-D-glucopyranose
XXXIII   Not shown
XXXIV 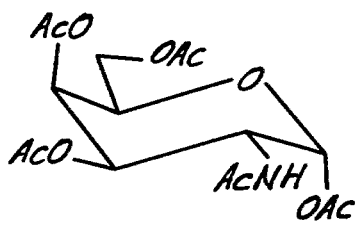
2-acetamido-1,3,4,6-tetra-O-acetyl-2-deoxy-α-D-galactopyranose
XXXV 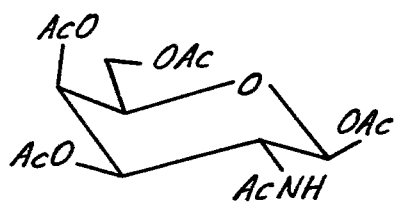
2-acetamido-1,3,4,6-tetra-O-acetyl-2-deoxy-β-D-galactopyranose Fig. 19.
XXXVI 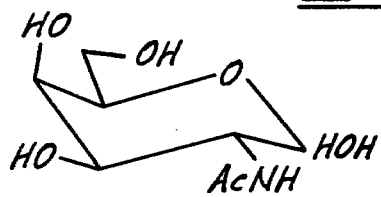 2-Acetamido-2-deoxy-D-galactose
XXXVII 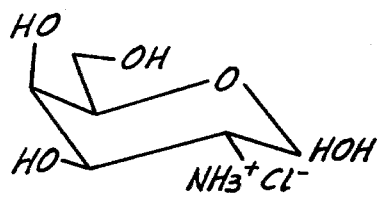 D-galactosamine hydrochloride
XXXVIII 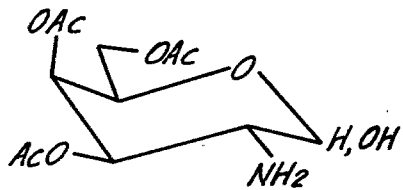 3,4,6-tri-O-acetyl-D-galactosamine
XXXIX 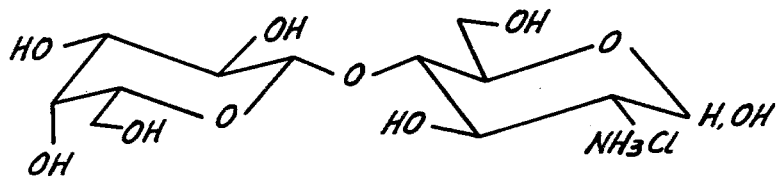
2-deoxy-D-lactosamine hydrochloride
XL 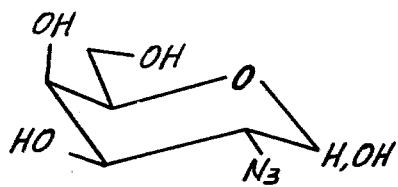 2-azido-2-deoxy-D-galactopyranose
XLI 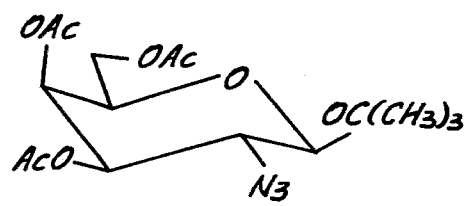
t-butyl-3,4,6-tri-O-acetyl-2-azido-2-deoxy-β-D-galactopyranoside

Fig.1h.
XLII
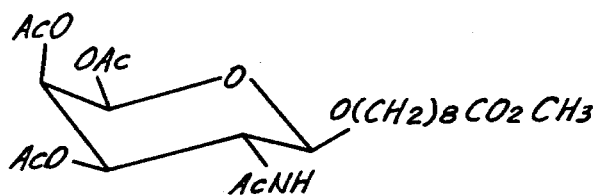
8-methoxyoctylcarbonyl-2-acetamido-3,4,6-tri-O-acetyl-2-deoxy-β-D-galactopyanoside
XLIII
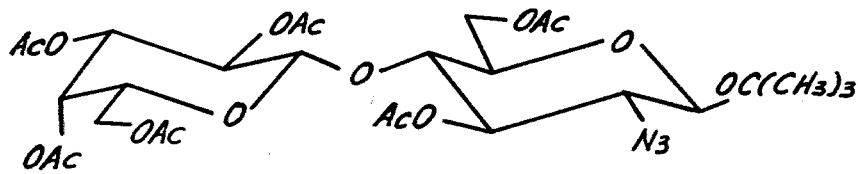
t-butyl-3,6-di-O-acetyl-4-O-(2,3,4,6-tetra-O-acetyl-β-D-galactopyranosyl)-2-azido-2-deoxy-β-D-glucopyranoside
XLIV
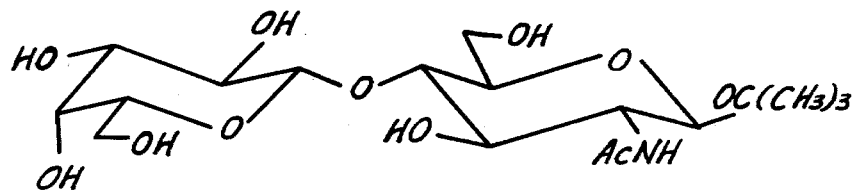
t-butyl-2-acetamido-2-deoxy-β-D-lactosyl glycoside
XLV
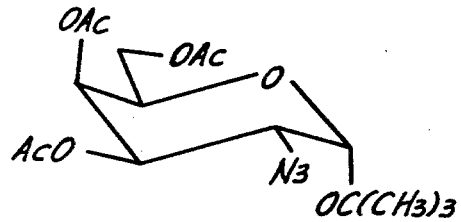
t-butyl-3,4,6-tri-O-acetyl-2-azido-2-deoxy-α-D-galactopyranoside Fig. 1i.
XLVI
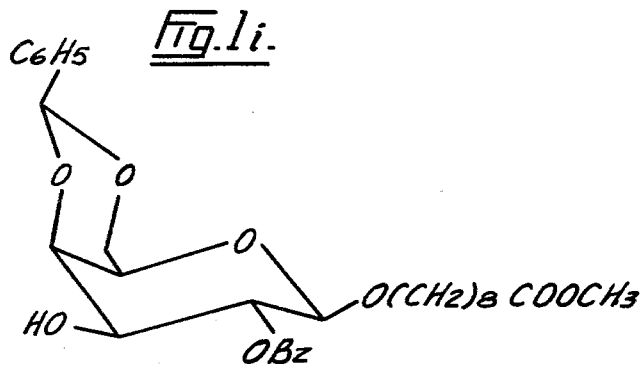
8-methoxycarbonyloctyl-4,6-O-benzylidene-2-O-benzoyl-β-D-galactopyranoside
XLVII
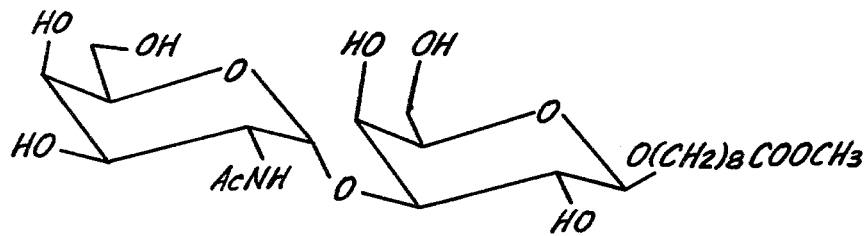
8 methoxycarbonyloctyl-3-O-(3,4,6-tri-O-acetyl-2-azido-2-deoxy-α-D-galactopyranosyl)-4,6-O-benzylidene-2-O-benzoyl-β-D-galactopyranoside
XLVIII
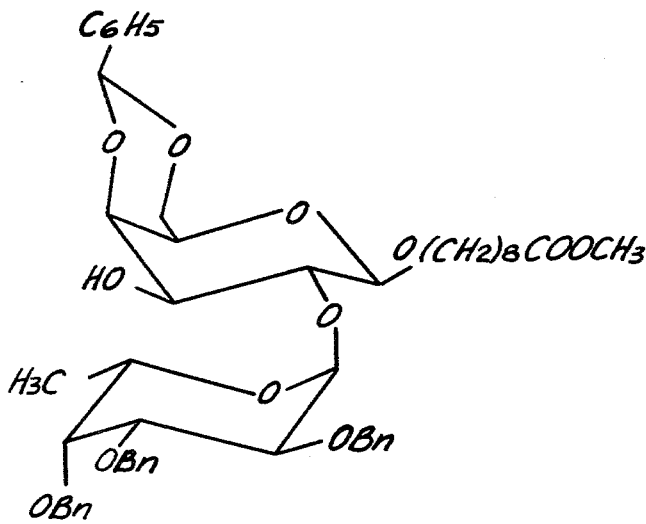
8 methoxycarbonyloctyl-2-O-(2,3,4-tri-O-benzyl-α-L-fucopyranosyl)-4,6-O-benzylidene-β-D-galactopyranoside Fig. 1j.
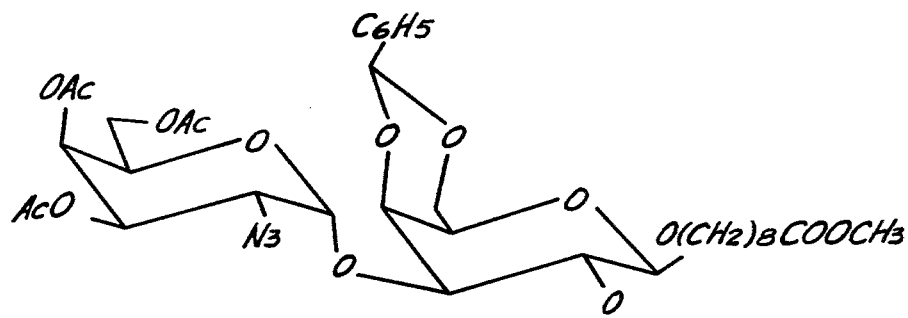
XLIX
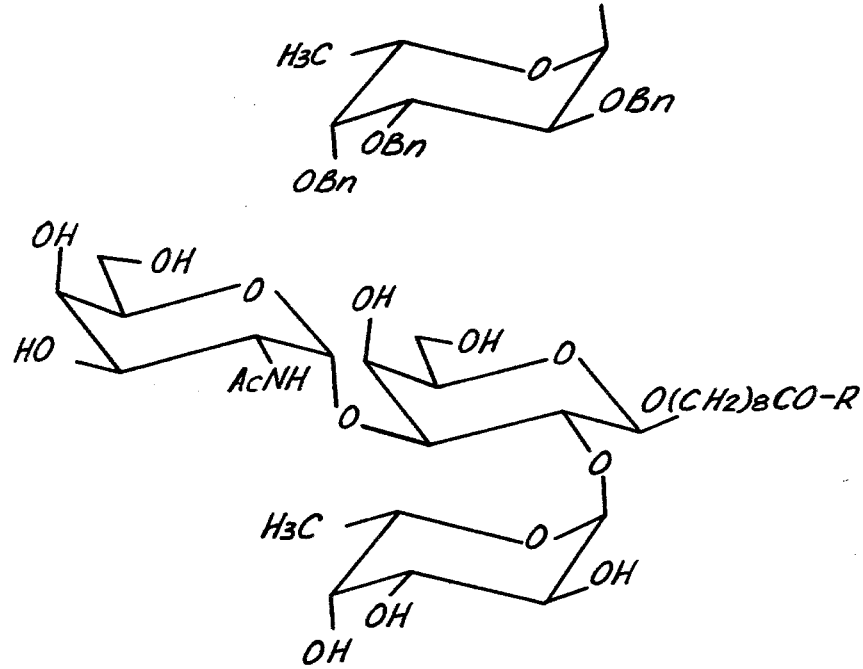
L    R = OCH₃
8-methoxycarbonyloctyl-3-O-(2-acetamido-2-deoxy-α-D-galactopyranosyl)-2-O-(α-L-fucopyranosyl)-β-D-galactopyranoside
LI    R = NH-NH₂
LII    R = carrier molecule
LIII    R = solid support

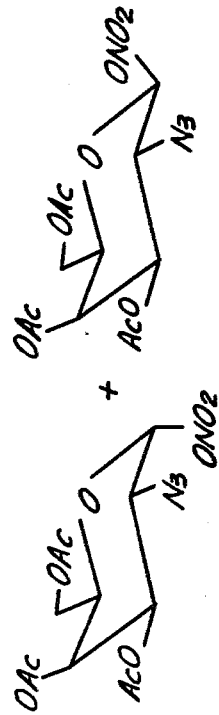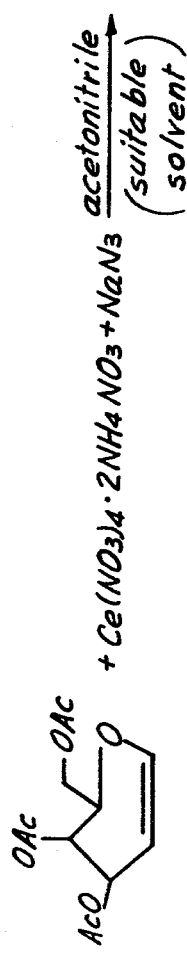
Fig. 2a.
Sample Reactions

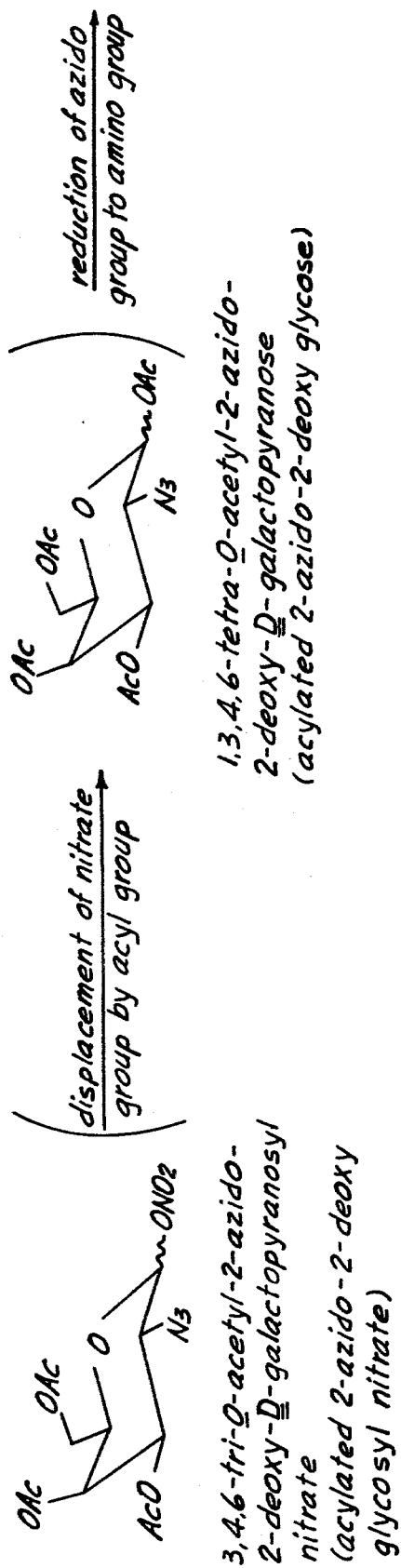
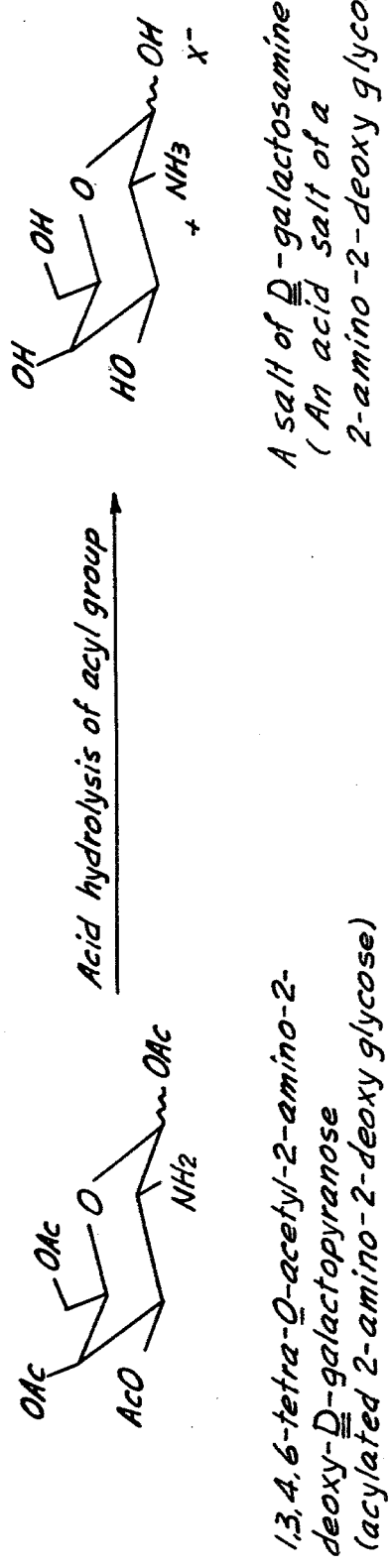
Fig. 2b.
CONVERSION OF AZIDONITRATES TO AMINOSUGARS

Fig. 2c.
Conversion of Azidonitrates to Azidohalides
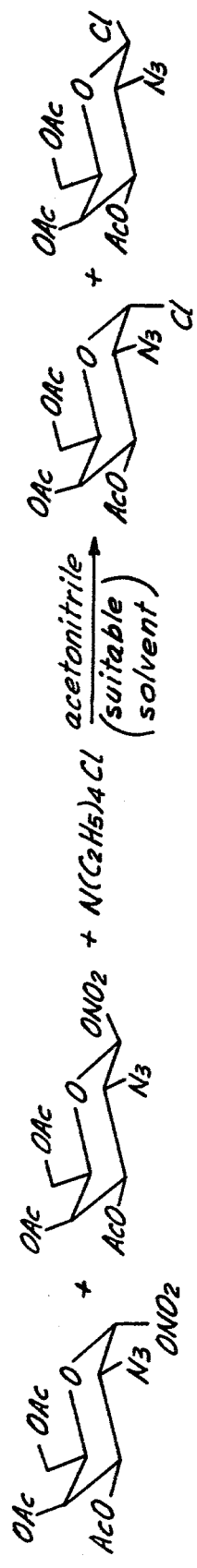

CONVERSION OF GLYCOSYL HALIDES TO GLYCOSIDES 3,4,6-tri-O-acetyl-2-azido-
2-deoxy-β-D-galactopyranosyl
chloride
(acylated 2-azido-2-deoxy glycosyl halide)

+ Ag₂CO₃ + CF₃SO₂O⁻Ag⁺ + (CH₃)₃COH silver       silver trifluoro-        t-butanol
carbonate    methanesulfonate         (alcohol)
(promoter)

t-butyl-3,4,6-tri-O-acetyl-2-
azido-2-deoxy-α-D-galactopyranoside
(acylated 2-azido-2-deoxy glycopyanoside)

SYNTHESIS OF 2-AMINO-2-DEOXYGLYCOSES AND 2-AMINO-2-DEOXYGLYCOSIDES FROM GLYCALS

BACKGROUND OF THE INVENTION

It is well known that carbohydrate structures of various complexities are the antigenic determinants for a wide range of substances. It is also well established that relatively small molecules, known as haptens, can correspond to the structure of the antigenic determinant. The hapten, when attached to an appropriate carrier molecule, provides an artificial antigen which, when administered to an animal under appropriate conditions, will give rise to the production of antibodies having a specificity for the hapten. Furthermore, in recent years, much art has developed for the preparation of immunoabsorbents from haptens. This art involves the attachment of the hapten, normally through covalent bonding but at times through hydrophobic bonding, to a solid, latex or gelatinous support. Thus, the hapten is immobilized so that when the resulting immunoabsorbent is exposed to antibodies with combining sites for the haptenic structure, the antibodies will attach themselves to the surface of the immunoabsorbent and thereby be specifically removed from solution.

Many varieties of solid, latex and gel supports for the preparation of immunoabsorbents have been developed and many ways have been devised for attachment of the hapten to these insoluble structures. Although improvements in these matters are possible, the main problem remains of having simple access to the desired hapten in a form convenient for attachment to the carrier molecule.

It was the original purpose of our work to develop a practical process for the synthesis of D-galactosamine hydrochloride (XXXVII) and of D-lactosamine hydrochloride (XXXIX) and derivatives of these. Both galactosamine and lactosamine, usually in the form of their N-acetylated derivatives, are found widespread in nature. They occur in glycoproteins, glycolipids and mucopolysaccharides. As such they are important building units found in the blood group substance antigenic determinants.

The main prior art source of D-galactosamine is the acid hydrolysis of chrondroitin sulfate C which is obtained by extracting cartilaginous tissues such as tendons, trachea and nasal septa. These yields are uncertain and it is difficult to obtain a crystalline product. Numerous chemical syntheses exist which include the opening of 1,6:2,3-dianhydro-β-D-talopyranose with ammonia or with azide ion. However, these methods involve six to eleven separate chemical transformations starting from the simple sugars. Shorter methods depend upon rather rare sugars as starting materials.

Inversion of the C-4 configuration of glucosamine through displacement of a 4-O-sulfonate of 2-acetamido-2-deoxy glucopyranosyl derivatives has also been utilized for the synthesis of D-galactosamine. However, the elaboration of glucosamine to the necessary starting material is tedious.

The synthesis of lactosamine is more difficult as it necessarily involves a glycosylation of a galactosyl halide with an elaborate derivative of 2-acetamido-2-deoxy-glucose. The most recently published method requires nine chemical transformations, starting from 2-acetamido-2-deoxy glucosamine, prior to the glycosylation step.

In accordance with a feature of the present invention, there is provided a reagent that allows efficient and high yield preparations of glycosides which contain the 2-acetamido-2-deoxy-α-D-galactopyranosyl group which is found, for example, in the antigenic determinant for the human A blood group and the Forssman antigen. The reagent thus claimed useful is 3,4,6-tri-O-acetyl-2-azido-2-deoxy-β-D-galactopyranosyl chloride (XXIII) prepared simply from D-galactal triacetate (I) in high yield.

It has long been anticipated that the use of a β-glycosyl halide would tend to yield the α-(1,2-cis)-glycosidic linkage through Walden inversion of the reacting center under Koenings-Knorr reaction conditions when the 2-substituent is so chosen as to not participate in a reaction at the anomeric center. Thus, for example, Wolfrom, Thompson and Linebeck (J. Org. Chem., 28, 860 (1963)) developed tri-O-acetyl-2-nitro-β-D-glucopyranosyl chloride for the purpose of synthesizing α-D-glucopyranosides. Indeed, several papers have appeared in the recent literature which utilize 2-azido-2-deoxy-β-D-glycopyranosyl chlorides such as is reported in processes of this invention leading to the formation of 2-azido-2-deoxy-α-D-galactopyranosides. However, it must be noted that the processes reported by Paulsen and co-workers (Angew. Chem., Int. Ed., 14, 558 (1975); Tet. Lett., 1493 (1975) and 2301 (1976); Angew. Chem., Int. Ed., 15, 440 (1975)) are of limited, if any commercial value in view of the extreme difficulty in achieving the synthesis of the desired 2-azido-2-deoxy reagent; namely, 6-O-acetyl-2-azido-3,4-O-benzyl-2-deoxy-β-D-galactopyranosyl chloride.

This invention reports a novel process for preparing efficiently the compound 3,4,6-tri-O-acetyl-2-azido-2-deoxy-β-D-galactopyranosyl chloride (XXIII) and its engagement in reactions with alcohol to form 3,4,6-tri-O-acetyl-2-azido-2-deoxy-α-D-galactopyranosides (A) under appropriate Koenings-Knorr type conditions for the condensation. The invention in

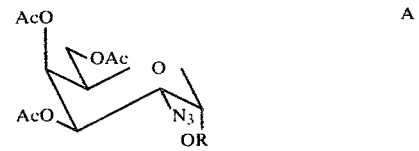

part concerns the discovery of processes that render compound XXIII a readily available reagent for use in reactions leading to products of type A. Thus, it has become commercially feasible to synthesize the terminal trisaccharide antigenic determinant for the human A-blood as is present in structures B for the type 1 and type 2 antigenic determinants for the human A blood group. The trisaccharide is synthesized in a form useful for the preparation of artificial antigens and immunoabsorbents related to the human A blood group.

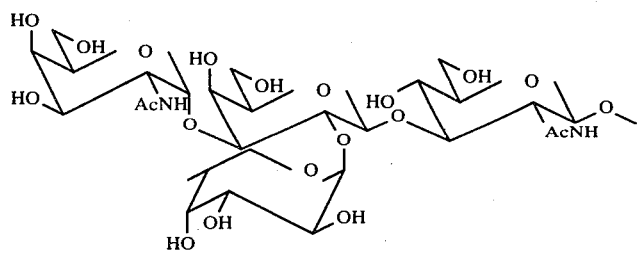

(Type 1 A Determinant)

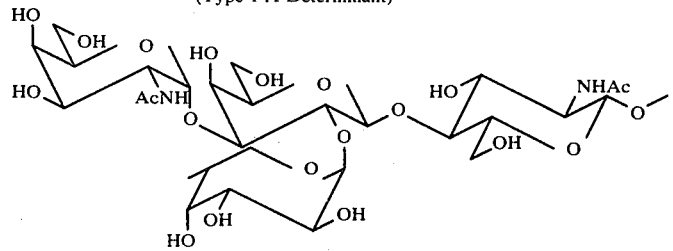

(Type 2 B Determinant)

The formation of α-azido-β-nitratoalkanes from the reaction of olefins with sodium azide and ceric ammonium nitrate has been reported by Trahanovsky and Robbins (J. Am. Chem. Soc., 93, 5256 (1971)). However the extension of the above reaction to vinylic ethers or structures as complex as D-galactal triacetate is not obvious. The base of this invention was the discovery that the addition of the azide and nitrate groups to 1,2-unsaturated sugars can be made to proceed in high economical yield to form the 2-azido-2-deoxy glycosyl nitrate.

SUMMARY OF THE INVENTION

In accordance with the basic aspect of the present invention, the treatment of protected glycals with azide ion in the presence of ceric ammonium nitrate results in the addition of an azide group and a nitrate group to the C-2 and C-1 positions, respectively, of the glycal. These novel products, namely the anomeric mixture of 2-azido-2-deoxy glycosyl nitrates, allow entrance into the following classes of compounds:

(1) the 2-amino-2-deoxy sugars by hydrolysis of the nitrate group and reduction of the azido group, (2) the 2-azido-2-deoxy glycosyl halides by displacement of the glycosyl nitrate, (3) the 2-amino-2-deoxy glycosides by reaction of the 2-azido-2-deoxy glycosyl halides. The virtue of the azido group is that it is a non-participating progenerator of an amino function and as such does not interfere with the synthesis of the 2-amino-2-deoxy-α-D-glycosides.

In accordance with a feature of the present invention, the 2-azido-2-deoxy glycosyl nitrates can be converted to the corresponding 2-amino-2-deoxy sugars by hydrolysis of the nitrate and protecting groups, and reduction of the azido group by methods well known to those skilled in the art. Hydrolysis may precede reduction or vice versa. N-acetylated derivatives of the amino sugars can be obtained by conventional methods.

In accordance with a further aspect of the present invention, the 2-azido-2-deoxy glycosyl nitrates may be treated with a halide salt to effect the displacement of the nitrate group and to produce the 2-azido-2-deoxy glycosyl halides, which are novel compounds. In a preferred procedure, by treating with iodide ion, an anomeric mixture of the glycosyl nitrates produces the thermodynamically more favorable anomer, 2-azido-2-deoxy-α-D-glycosyl iodide. The α-glycosyl iodide is readily displaced with one equivalent of chloride ion through inversion to give in high yields the 2-azido-2-deoxy-β-D-glycosyl chloride. This route to the β-halide is advantageous as it allows conversion of the nitrates to a reaction product which comprises predominantly the 2-azido-2-deoxy-β-D-galactosyl chloride, which is useful for the formation of a 2-deoxy-α-D-glycoside, an integral unit of the A blood group determinant. The reagent thus claimed useful is 3,4,6-tri-O-acetyl-2-azido-2-deoxy-β-D-galactopyranosyl chloride (XXIII).

The 2-azido-2-deoxy glycosyl halides may be used to prepare 2-amino-2-deoxy glycosides under conditions for glycosidation, such as those generally known in carbohydrate chemistry as Koenings-Knorr conditions. These reactions involve the treatment of the glycosyl halide with an alcohol in the presence of a promoter to effect the replacement of the halogen by the alkoxy group of the alcohol. The 2-azido-2-deoxy glycoside, thus obtained, is reduced by methods well known to persons skilled in the art to obtain the 2-amino-2-deoxy glycosides. In addition, the protecting groups can be removed in order to deblock the glycoside. Specifically, 3,4,6-tri-O-acetyl-2-azido-2-deoxy-β-D-galactopyranosyl chloride may be reacted with 8-methoxycarbonyloctyl-2-O-(2,3,4-tri-O-benzyl-α-L-fucopyranosyl)-4,6-O-benzylidene-β-D-galactopyranosyl in the presence of a promoter. The trisaccharidic product is deblocked and its azido group is reduced to the amine which is subsequently acetylated to give 8-methoxycarbonyloctyl-3-O-(2-acetamido-2-deoxy-α-D-galacto pyranosyl)-2-O-(α-L-fucopyranosyl)-β-D-galactopyranoside. This latter product corresponds to the antigenic determinant for the human A blood group and can be used to prepare an immunoabsorbent specific for the anti-A antibodies by attachment to an insoluble support. Also, this latter product can be used to inhibit the reaction between anti-A antibodies and human A erythrocytes. Furthermore, the product can be used to prepare artificial antigens which allow the raising, through immunization, of monospecific anti-A antibodies in test animals. The subsequent isolation of these antibodies using the immunoabsorbent then provides an important and useful reagent for cell and tissue typing.

The slight excess of reagent is used to compensate for this loss.

Without being bound by the same, the following mechanism is suggested for the azidonitration reaction:

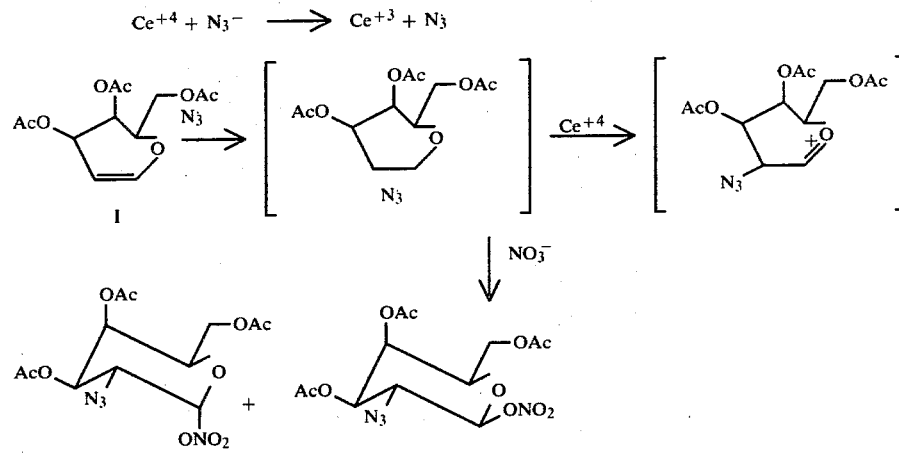

DESCRIPTION OF THE DRAWINGS

FIG. 1 is a formula sheet showing structure formulas and names for compounds referred to by number in the specification.

DESCRIPTION OF THE PREFERRED EMBODIMENT OF THE INVENTION

Figure 2D:
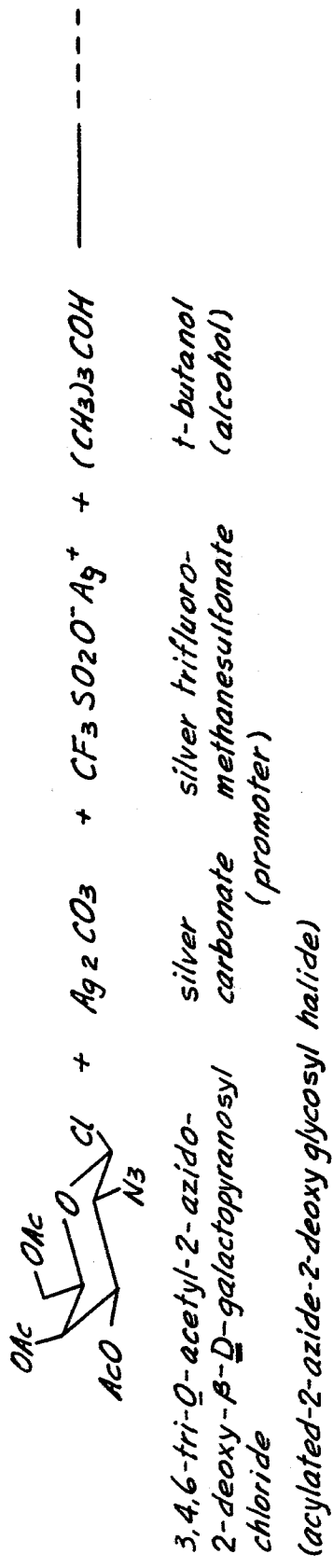
FIG. 2 is a reaction sheet showing examples of the reactions described in the specification.

The Azidonitration Reaction:

The Formula Sheet provides structural formulas for compounds I to LII. Reference is made to these compounds in the course of this description and in specific experimental examples which demonstrate the invention.

Examples I through VII show the reaction of suitably protected glycals with ceric ammonium nitrate and an azide salt to form the corresponding 2-azido-2-deoxy glycosyl nitrates.

The term glycal applies to 1,2-unsaturated sugars which are characterized by the structural entity

The term protected glycal denotes that the hydroxyl substituents have been masked by blocking groups such as acetyl, propionyl, and benzoyl which, being less reactive than the hydroxyl group, will not participate in subsequent reactions. In this manner, the properties of the glycal other than those of the unsaturation will be retained.

Examples of protected glycals are 3,4,6-tri-O-acetyl-D-galactal, I; 3,4,6-tri-O-acetyl-D-glucal, VI; 3,4,6-tri-O-benzoyl-D-galactal, X; hexa-O-acetyl-D-lactal, XIII; and 3,4-di-O-acetyl-D-xylal, XVI.

In the azidonitration of glycals, demonstrated in Examples I through VII, the protected glycals are reacted with an excess of a 2:1 (mole/mole) mixture of ceric ammonium nitrate and an azide salt. It is known that these two salts react to form nitrogen gas as a product.

Ce(IV) is a strong oxidizing agent and strips an electron from the negatively charged azide ion. The resulting azide radical adds across the 1,2-unsaturated bond of the glycal to form an intermediate radical. A second Ce(IV) ion may oxidize the intermediate radical to give an oxycarbonium. The addition of a nitrate ion, to the C-1 position, results in the 2-azido-2-deoxy glycosyl nitrate.

The azide salt may be any of the common alkali metal azides. Sodium azide is used, preferably for reasons of cost and handling, but the lithium or potassium azides are also suitable.

A 2-azido substituent is desirable as it will not interfere in the subsequent formation of a α-glycosidic linkage at the anomeric (C-1) center and can be reduced to an amino function by well known methods to produce 2-amino-2-deoxy sugars.

A solvent is used which is able to dissolve the three reagents, the nonpolar glycal and the ionic salts, at a level to provide sufficient concentrations of these in the reaction mixture. In addition, the solvent should be substantially inert to reaction and resistant to oxidation by the ceric salt. The preferred solvent is acetonitrile because of its resistance to oxidation and its ability to provide appropriate concentrations of the reacting species in solution. Other solvents can be used such as ethyl acetate or acetic acid, but side reactions are rather severe in the case of the latter. The solvent is preferably dried prior to use as the presence of water was found to support side reactions.

Due to the dissimilarity in the solubility of the reactants, effective stirring is required to maintain sufficient concentrations in the reaction mixture and to ensure an efficient rate of reaction.

The preferred reaction temperature range is from −25° C. to +25° C. The lower limit was determined by the freezing point of the acetonitrile, the solvent preferentially used; while the upper limit was arbitrarily chosen as a cutoff above which competing side reactions became significant. Although the reaction kinetics were slower at lower temperatures, giving rise to longer reaction times, the yields of the desired products were better.

Although the reaction can be performed in air, an inert atmosphere, such as nitrogen, is preferably used.

Examples I and II illustrate two different techniques, within the scope of the present invention, for preparing the 2-azido-2-deoxy nitrates of 3,4,6-tri-O-acetyl-D-galactal. The first is a process which is attractive to commercial production while the second describes the experiment which led to the discovery. It is within the scope and spirit of this invention to claim all those variations in the reaction conditions and work-up procedures that are evident to chemists competent to consider and to test the effectiveness of alternate procedures which would involve such variations as changes in reaction and extracting solvents, modes of addition, stirring rates and temperature range.

EXAMPLE I

The reaction of 2,3,4-tri-O-acetyl-D-galactal (I) with ceric ammonium nitrate in the presence of sodium azide A three-necked, five liter, round bottom flask equipped with an inlet tube, exhaust tube and an efficient mechanical stirrer was charged with solid ceric ammonium nitrate (899.90 g., 1.64 mole) and solid sodium azide (53.37 g, 0.82 mole) and cooled to $-15°$ C. under a nitrogen atmosphere. 2,3,4-tri-O-acetyl-D-galactal(I)(150 g, 0.551 mole) was dissolved in anhydrous acetonitrile (3.4 l) in a three-necked, four-liter flask equipped with an inlet and an outlet tube. This solution was cooled to $-15°$ C. while sweeping with nitrogen. By applying a positive pressure of nitrogen the acetonitrile solution was pumped into the vessel containing the solid reactants via an inert tube. After complete addition of the acetonitrile solution (approximately 1 minute), mechanical stirring was commenced and continued for approximately 15 to 20 hours or until such time as no glycal remained on examination of the reaction mixture by thin layer chromatography (t.l.c.) on silica gel eluted with hexane-ethyl acetate (v/v) 6:4. At that time toluene (1 l) and cold water (1 l) were added and the reaction vessel was removed from the cooling bath. This mixture was transferred to a ten-liter container and after addition of toluene (2 l) the organic layer was separated and transferred to a separatory funnel. This solution was washed with cold water ($3 \times 1$ l). The organic layer was filtered through toluene-wetted filter paper and the filtrate was concentrated in vacuo at a temperature below 40° C. to a syrup (200 g). The proton magnetic resonance (p.m.r.) spectrum of this syrup showed it to be composed mainly of 2-azido-2-deoxy nitrates. The composition of the product was 37% of 3,4,6-tri-O-acetyl-2-azido-2-deoxy-$\alpha$-D-galactopyranosyl nitrate (II), 55% of 3,4,6-tri-O-acetyl-2-azido-2-deoxy-$\beta$-D-galactopyranosyl nitrate (III) and 8% of 3,4,6-tri-O-acetyl-2-azido-2-deoxy-$\alpha$-D-talapyranosyl nitrate (IV).

The low yield of compound IV indicates that the azidonitration reaction is highly stereoselective at the C-2 position.

Trituration of a portion of the syrupy product (21.0 g) with cold ethyl ether gave compounds II and IV (8.3 g) which co-crystallized. The mother liquor contained almost pure $\beta$-D-nitrate, III, (12.6 g). Compound III could not be crystallized. The infrared (i.r.) spectrum (film) of compound III displayed absorbances at 2120 cm$^{-1}$(N$_3$) and 1650 cm$^{-1}$ (ONO$_2$); its partial p.m.r. spectrum in CDCl$_3$ was, ppm 5.71 (d, 1, J$_{1,2}$ 9.0 Hz, H-1), 5.42 (q, 1, H-4), 5.08 (q, 1, J$_{3,4}$ 3.2 Hz, H-3), 3.87 (q, 1, J$_{2,3}$ 10.8 Hz, H-2), 2.18, 2.10, 2.03 (3s, 9, 3 OAC).

Compound II, free of the talo azide (IV), was obtained by anomerization of the $\beta$-D-nitrate, III, with nitrate ion. A solution of the syrupy $\beta$-D-nitrate, III, (9.50 g, 25.5 mmole) and anhydrous lithium nitrate (3.50 g, 50.1 mmole) in 4:1 (v/v) acetonitrile:dimethylformamide (35 ml) was stirred for 42 hours at ambient temperature, after which time it was diluted with dichloromethane (250 ml) and washed with ice cold water ($3 \times 125$ ml). The organic solution was dried and evaporated to give a syrup (9.0 g). The p.m.r. spectrum of this syrup showed it to be a mixture of 63% $\alpha$- and 37% $\beta$-D-nitrates, II and III. Crystallization from ethyl ether gave the $\alpha$-D-nitrate, II, (6.2 g), m.p. 103°-104° C., $[\alpha]_D^{25} +125°$ (c 1, chloroform). The infrared spectrum (film) of compound II displayed absorbances at 2120 cm$^{-1}$ (N$_3$) and 1650 cm$^{-1}$ (ONO$_2$); its partial p.m.r. spectrum in CDCl$_3$ was, p.p.m. 6.34 (d, 1, J$_{1,2}$ 4.1 Hz, H-3), 4.12 (q, 1, J$_{2,3}$11.5 Hz, H-2); 2.18, 2.09, 2.02 (3s, 3 OAC).

A minor side product (<10%) of the reaction could be isolated either by chromatography on silica gel of the reaction mixture or, in some cases, by evaporation of the three aqueous washings obtained during the reaction product workup described above. The compound readily crystallized from the washings by evaporation or upon trituration with ethyl ether, and was shown to be N-(3,4,6-tri-O-acetyl-2-azido-2-deoxy-$\alpha$-D-galactopyranosyl) acetamide (V); m.p. 142°-143.5° C., $[\alpha]_D^{25} +68.0°$ (c 1, chloroform). Its partial p.m.r. spectrum in DMSO-d$_6$ was, p.p.m. 9.83 (d, 1, J$_{NH,1}$ 9.5 Hz, NH), 5.78 (q, 1, J$_{1,2}$ 5.5 Hz, H-1), 5.48 (1, q, J$_{2,3}$ 11.3 Hz, H-3), 5.22 (1, d, J$_{3,4}$ 3.5 Hz, H-4), 4.22 (q, 1, H-2).

EXAMPLE II

The reaction of 3,4,6-tri-O-acetyl-D-galactal (I) with ceric ammonium nitrate in the presence of sodium azide.

Distilled 2,3,4-tri-O-acetyl-D-galactal (I) (21.1 g, 0.007 M) (b.p. 147°-155° at 0.1 mm) was dissolved in dry acetonitrile (420 ml) and cooled to $-25°$ C. under a nitrogen atmosphere in the dark. A mixture of solid ceric ammonium nitrate (100.2 g, 0.182 mole) and solid sodium azide (6.043 g, 0.092 mole) was added all at once and the resulting suspension was stirred for 15 hours at $-25°$ C. At this time cold ethyl ether (400 ml) was added and the resulting mixture filtered to remove any solids. The filter cake was washed with diethyl ether ($2 \times 100$ ml) and the combined filtrate was poured into ice water (500 ml). The organic solution was separated and washed with ice cold water ($3 \times 500$ ml), dried over anhydrous sodium sulfate, filtered and evaporated to give a syrup (21.0 g), which corresponded to a 73% yield of the crude nitrates (II and III). Thin layer chromatography examination on silica gel developed with 6:4 (v/v) hexane:ethyl acetate showed no remaining starting material. P.m.r. examination showed the product to be essentially identical to the syrupy product obtained in Example I.

Because of the reactivity of glycosyl nitrates in general, care must be exercised in the handling of these compounds so as to not effect undesired decomposition or solvolytic reactions. The mixture of $\alpha$- and $\beta$-nitrates obtained may vary since, as is demonstrated in Example I, the compounds are readily interconverted in the presence of nitrate ion. The mixture is as useful as either of the pure products for the purposes of this invention, as will be demonstrated later. In general, no effort is made to separate the compounds (II and III). However, it was found that the α-anomer (III) is readily obtained in the crystalline state and if this substance is desired, the yield can be improved by anomerization of the β-anomer which is the thermodynamically less stable compound.

The azidonitration reaction demonstrated in Example I is not restricted to the acetylated galactal, I, but finds useful application with suitably O-protected glycals in general. This is demonstrated by Example III wherein the selected reactant is tri-O-acetyl-D-glucal, (VI), a different hexal, and further exemplified through the use of hexa-O-acetyl-D-lactal (XIII), having a disaccharide structure, in Example IV and of 3,4-di-O-acetyl-D-xylal (XVI), a pental, in Example V.

Further, Example III illustrates that the temperature at which the reaction is conducted may be varied although product purity decreases at reaction temperatures above 0° C. The use of potassium azide is also demonstrated.

EXAMPLE III

The reaction of 3,4,6-tri-O-acetyl-D-glucal (VI) with ceric ammonium nitrate in the presence of potassium azide Treatment of 2,3,4-tri-O-acetyl-D-glucal (VI) (5.86 g, 21.5 mmole) with ceric ammonium nitrate (27.8 g, 50.7 mmole) and potassium azide (2.39 g, 25.7 mmole) at 25° C. by the method of Example I for tri-O-acetyl-D-galactal, gave a mixture of 2-azido nitrates in 60% yield. Of the azido nitrate products, this mixture was shown to be composed of 3,4,6-tri-O-acetyl-2-azido-2-deoxy-β-D-glucopyranosyl nitrate (VIII) 42.5%, 3,4,6-tri-O-acetyl-2-azido-2-deoxy-α-D-glucopyranosyl nitrate (VII) 24%, and 3,4,6-tri-O-acetyl-2-azido-2-deoxy-α-D-mannopyranosyl nitrate (IX) 33%. This composition was based on the relative intensities of the p.m.r. anomeric signals assigned to compounds VII, IX, and VIII which were at 6.4 p.p.m., J=4.0 Hz, 6.28 p.p.m., J=1.8 Hz and 5.72 p.p.m., J=8.8 Hz, respectively.

EXAMPLE IV

The reaction of hexa-O-acetyl-D-lactal (XIII) with ceric ammonium nitrate in the presence of sodium azide The azidonitration of hexa-O-acetyl-D-lactal (XIII) serves as a new route to the important disaccharide known as a lactosamine and which is a building block of oligosaccharides which form the core structure of oligosaccharides found in human milk and the antigenic structures of the human blood group substances.

Treatment of hexa-O-acetyl-D-lactal (XIII) (1.0 g, 1.79 mmole) with ceric ammonium nitrate (2.45 g, 4.48 mmole) and sodium azide (0.174 g, 2.685 mmole) by the method of Example II gave a mixture of the 2-azido nitrates (0.89 g) in greater than 75% yield. P.m.r. examination showed signals at 6.30 p.p.m. (d, 4.25 Hz) and 5.56 p.p.m. (d, 8.5 Hz) which were assigned to the anomeric protons of the 2-azido nitrates XIV and XV, respectively. Trituration of this syrup with ethyl ether gave crystalline 3,6-di-O-acetyl-4-O-(2,3,4,6-tetra-O-acetyl-β-D-galactopyranosyl)-2-azido-2-deoxyl-β-D-glucopyranosyl nitrate (XV) (0.5 g) in 42% yield: m.p. 69°–70°; [α]$_D^{25}$+15° (c 1, chloroform). The infrared spectrum (nujol mull) of compound XV displayed absorbances at 2120 cm$^{-1}$(N$_3$) and 1650 cm$^{-1}$ (ONO$_2$); it partial p.m.r. in CDCl$_3$ was, p.p.m. 5.56 (d, 1, J$_{1,2}$ 8.5 Hz, H-1), 3.56 (q, 1, J$_{2,3}$ 8.25 Hz, H-2).

Column chromatography of the mother liquor, after the removal of crystalline compound XV, on silica gel developed with hexane-ethyl acetate-ethanol (v/v) 10:10:1 afforded additional quantities of compound XV (0.05 g) and 3,6-di-O-acetyl-4-O-(2,3,4,6-tetra-O-acetyl-β-D-galuctopyranosyl)-2-azido-2-deoxy-α-D-glucopyranosyl nitrate (XIV) (0.31 g) which was crystallized from ethyl ether: m.p. 138°–140°; [α]$_D^{25}$+69.7° (c 1, chloroform). The infrared spectrum (nujol mull) of compound XIV displayed absorbances at 2120 cm$^{-1}$ (N$_3$) and 1650 cm$^{-1}$ (ONO$_2$); its partial p.m.r. spectrum in CDCl$_3$ was, p.p.m. 6.30 (d, 1, J$_{1,2}$ 4.25 Hz, H-1), 3.72 (q, 1, J$_{2,3}$ 10.5 Hz, H-2).

EXAMPLE V

The reaction of 3,4-di-O-acetyl-D-xylal (XVI) with ceric ammonium nitrate in the presence of sodium azide Example V shows that the application of the process of azido nitration can be extended to the pentopyranoglycals.

Treatment of di-O-acetyl-D-xylal (XVI) (29) (0.472 g, 2.36 mmoles) with ceric ammonium nitrate (4.39 g, 8.0 mmoles) and sodium azide (0.260 g, 4.0 mmoles) by the method described in Example II gave a mixture of 2-azido-nitrates in 88% yield. P.m.r. examination of the product mixture showed signals at 5.70 p.p.m. (d, 7.5 Hz), 68%, 6.28 p.p.m. (d, 4.0 Hz), ≃16%, and 6.56 p.p.m. (d, 4.5 Hz), ≃16%. The major product was shown to be 3,4-di-O-acetyl-2-azido-2-deoxy-β-D-xylopyranosyl nitrate XVII by double irradiation experiments which showed the presence of a quartet at 3.70 p.p.m., with J$_{2,3}$=8.75 Hz and J$_{1,2}$=7.5 Hz, which was assigned to H-2 of compound XVII. The products comprising the remaining 32% of the mixture of 2-azido-2-deoxy-nitrates must be the α and β-D-lyxo anomers XVIII as anomerization of the mixture of nitrates, by the method described in Example I for compound III, caused the appearance of a new signal in the p.m.r. spectrum of this product mixture, at 6.31 p.p.m. (d, J$_{1,2}$ 3.65 Hz). This signal is attributed to the anomeric proton of 3,4-di-O-acetyl-2-azido-2-deoxy-α-D-xylopyranosyl nitrate (XVIX).

EXAMPLE VI

The reaction of 3,4,6-tri-O-benzoyl-D-galactal (X) with ceric ammonium nitrate in the presence of sodium azide The azidonitration reaction is not restricted to acetylated glycals but can be applied to any suitably protected glycal. For example, the blocking groups may be propionyl or benzoyl. This is demonstrated in this example wherein 3,4,6-tri-O-benzoyl-D-galactal (X) is used as the starting material.

Treatment of 3,4,6-tri-O-benzoyl-D-galactal (X) (7.18 g, 12.2 mmole) with ceric ammonium nitrate (20.2 g, 36.6 mmole) and sodium azide (1.18 g, 18.1 mmole) by the method described in Example I for tri-O-acetyl-D-galactal gave a mixture of 2-azido-2-deoxy-nitrates (7.5 g) in 75% yield. Examination of the p.m.r. spectrum of the crude product in CDCl$_3$ showed it to be composed of 2-azido-3,4,6-tri-O-benzoyl-2-deoxy-α-D-galactopyranosyl nitrate (XI) (30%) and 2-azido-3,4,6-tri-O-benzoyl-2-deoxy-β-D-galactopyranosyl nitrate (XII) (45%). The anomeric signal of the α-D-nitrate was observed at 6.67 p.p.m. with J$_{1,2}$=4.6 Hz. Although the anomeric signal of the β-D-anomer was masked, the H-2 signal was observed at 4.20 p.p.m. as a large triplet with J$_{1,2}$=9.5 Hz.

EXAMPLE VII

Reaction of 3,4,6-tri-O-acetyl-D-galactal with sodium azide and ceric ammonium nitrate in ethyl acetate Although acetonitrile is the preferred solvent, the azidonitration reaction is not restricted to the choice of this solvent. This is demonstrated by this example wherein ethyl acetate is used as the solvent.

Treatment of tri-O-acetyl-D-galactal (I) (0.30 g, 1.09 mmole) with ceric ammonium nitrate (1.41 g, 2.57 mmole) and sodium azide (0.084 g, 1.29 mmole) in ethyl acetate (5 ml) by the method described in Example I gave a mixture of the 2-azido nitrates in greater than 60% yield. P.m.r. examination of the product showed the 2-azido-nitrate composition to be similar to that described in Example I. However, examination by thin layer chromatography on silica gel, developed with 6:4 (v/v) hexane:ethyl acetate, gave evidence that more side reactions had occurred in this solvent.

Conversion of Azidonitrates to Aminosugars

The acylated 2-azido-2-deoxy nitrates can be converted to the corresponding 2-amino-2-deoxy sugars by hydrolysis of the nitrate and acyl groups and reduction of the azido group by methods well known to those skilled in the art. Hydrolysis may precede reduction or vice versa. The aminosugars, in particular galactosamine and lactosamine and their N-acetylated derivatives are important building units for the blood group substance antigenic determinants. The N-acetylated derivatives are prepared from the aminosugar by methods well known to those skilled in the art. The aminosugars may also be used to prepare the 2-acetamido-2-deoxyglycoses.

Reduction of azido groups to amino groups is well known and can be conducted in virtually quantitative yield under a wide variety of conditions including reductions with metals such as sodium or zinc, reduction by catalytic hydrogenation using such catalysts as nickel, platinum or palladium, reduction using hydrides such as sodium borohydride, borane and lithium aluminum hydride, electrolytic reductions and reduction by hydrogen sulfide under alkaline conditions.

Broadly stated, the invention provides a process for converting an acylated 2-azido-2-deoxy glycosyl nitrate to a 2-amino-2-deoxy glycose which comprises reducing the azido group to an amino group and hydrolyzing the acyl and nitrate groups.

The nitrate groups of the acylated 2-azido-2-deoxynitrate may be displaced with an acyl group by conventional methods prior to hydrolysis or reduction. For example, the nitrate compound may be treated with sodium acetate in acetic acid as illustrated in Examples XIV-XVI.

EXAMPLE VIII

Preparations of the anomeric 1,3,4,6-tetra-O-acetyl-2-azido-2-deoxy-D-galactopyranoses (XXVII) and (XXVIII)

A solution of the pure 3,4,6-tri-O-acetyl-2-azido-2-deoxy-β-D-galactopyranosyl nitrate (III) (0.15 g, 0.40 mmole) and sodium acetate (0.65 g, 0.80 mmole) in glacial acetic acid (2 ml) was heated to 100° for 15 minutes at which time examination by thin layer chromatography of silica gel developed with 6:4 (v/v) hexane:ethyl acetate showed one homogeneous spot of lower $R_f$ than compound III. The solution was diluted with dichloromethane (5 ml) and washed with ice cold water (5 ml). Evaporation of the solvent, after drying over sodium sulfate and filtration, gave a syrup (0.134 g, 90% yield), which spontaneously crystallized upon trituration with ethyl ether.

Recrystallization from ethyl ether or cold ethanol gave an analytically pure sample of 1,3,4,6-tetra-O-acetyl-2-azido-2-deoxy-α-D-galactopyranose (XXVII), m.p. 114°-115°, $[\alpha]_D^{25} + 91.70$ (c 1.05, chloroform), i.r. (film) 2120 cm (—N$_3$).

The p.m.r. spectrum of compound XXVII in CDCl$_3$ showed, in part, p.p.m. 6.38 (d, 1, $J_{1,2}$ 3.7 Hz, H-1), 5.50 (q, 1, $J_{3,4}$ 3 Hz, H-4), 5.36 (q, 1, $J_{2,3}$ 7 Hz H-3), 3.97 (q, 1, H-2).

A solution of the crude 3,4,6-tri-O-acetyl-2-azido-2-deoxy-α-D-galactopyranosyl nitrate II (1.01 g, 2.70 mmole) and sodium acetate (0.43 g 5.20 mmole) in glacial acetic acid (10 ml) was heated to 100° for 20 minutes. The reaction solution was then diluted with dichloromethane (50 ml) and washed with ice cold water (250 ml). Evaporation of the solvent, after drying over sodium sulfate and filtration, gave syrup (1.0 g). Inspection of this syrup by p.m.r. spectroscopy showed it to be composed of compound XXVII (30%) and 1,3,4,6-tetra-O-acetyl-2-azido-2-deoxy-β-D-galactopyranose XXVIII (60%). The anomeric proton of the β-anomer (XXVIII) was assigned to a doublet, with J=8.5 Hz, at 5.61 p.p.m.

Compounds XXVII and XXVIII were obtained in a near 3:1 mixture by acetolysis in acetic acid containing sodium acetate of the mixture of compounds II and III obtained by way of the process described in Example II.

EXAMPLE IX

Preparations of 1,3,4,6-tetra-O-acetyl-2-azido-2-deoxy-α-D-gluco and manopyranoses (XXIX and XXX)

A mixture of 3,4,6-tri-O-acetyl-2-azido-2-deoxy-β-D-mannopyranosyl nitrate (IX) and the α- and β- anomers of 3,4,6-tri-O-acetyl-2-azido-2-deoxy-D-glucopyranosyl nitrate (VII and VIII), obtained as described in Example III, was treated with a solution of sodium acetate (0.350 g, 4.26 mmoles) in acetic acid (10 ml) at 100° C. for one hour. Work up of the product mixture by the method of Example II gave a foam (0.70 g). Column chromatography (30×2 cm) on silica gel (70 g) eluted with hexaneethyl acetate-ethanol (v/v) 10:10:1 afforded the separation of the gluco-(XXIX) and mano(XXX) 2-azido-2-deoxy acetates, 0.340 g and 0.310 g respectively.

Pure 1,3,4,6-tetra-O-acetyl-2-azido-2-deoxy-α-D-glucopyranose (XXIX) (0.211 g, 21%) was obtained by recrystallization from ethyl ether; m.p. 117°-118° C., $[\alpha]_D^{25} + 128°$ (c 0.9, chloroform). The partial p.m.r. spectrum of compound XXIX in CDCl$_3$ gave, p.p.m. 6.29 (d, 1, $J_{1,2}$ 3.5 Hz, H-1), 5.45 (t, 1, $J_{3,4}$ 9.0 Hz, H-3), 5.08 (t, 1, $J_{4,5}$ 9.0 Hz, H-4), 3.65 (q, 1, $J_{2,3}$ 9.0 Hz, H-2).

Pure 1,3,4,6-tetra-O-acetyl-2-azido-2-deoxy-α-D-mannopyranose (XXX) (0.220 g, 22%) was obtained by recrystallization from ethyl ether; m.p. 131°-132° C., $[\alpha]_D^{25} + 78.6$ (c 1.02, chloroform). The partial p.m.r. spectrum of compound XXX in CDCl$_3$ gave, p.p.m. 6.09 (d, 1, $J_{1,2}$ 1.8, H-1).

EXAMPLE X

Preparations of the anomeric forms of 1,3,6-tri-O-acetyl-4-O-(2,3,4,6-tetra-O-acetyl-β-D-galactopyranosyl)-2-azido-2-deoxy-D-glucopyranose (XXXI and XXXII)

Treatment of an anomeric mixture of 3,6-di-O-acetyl-d-O-(2,3,4,6-tetra-O-acetyl-β-galactopyranosyl)-2-azido-2-deoxy-D-glucopyranosyl nitrate (XIV and XV) comprising about 70% of the β-anomer (XV) (3.50 g) with sodium acetate (2.16 g, 26.3 mmole) in acetic acid by the method described in Example XV gave crystalline 1,3,6-tri-O-acetyl-4-O-(2,3,4,6-tetra-O-acetyl-β-D-galactopyranosyl)-2-azido-2-deoxy-α-D-glucopyranose (2.48 g) (XXXI) in 73% yield. Recrystallization from ethyl acetate-pentane gave the pure α-anomer (XXXI), m.p. 77°–78° C., $[\alpha]_D^{25}+55.4°$ (c 1, chloroform). The partial p.m.r. spectrum of compound XXXI in CDCl$_3$ was, p.p.m. 6.22 (d, 1, $J_{1,2}$ 3.65, H-1), 3.46 (q, 1, $J_{2,3}$ 10.5, H-2).

Similar treatment of the pure α-nitrate, XIV, in the manner described above gave crystalline 1,3,6-tri-O-acetyl-4-O-(2,3,4,6-tetra-O-acetyl-β-D-glucopyranose (XXXII) in good yield (70%).

Excellent yields of compound XXXII were also obtained by the treatment of 3,6-di-O-acetyl-4-O-(2,3,4,6-tetra-O-acetyl-β-D-galactopyranosyl)-2-azido-2-deoxy-α-D-glucopyranosyl chloride (XXV) (0.264, 0.414 mmoles) or of the corresponding α-bromide, XXVI, with silver acetate (0.137 g, 1.656 mmoles) in acetic acid (5 ml) at ambient temperature for one hour. At that time, the reaction solution was diluted with dichloromethane (20 ml), filtered and washed with water (2×20 ml). The organic layer was dried and evaporated to give a white foam (0.250 g). Crystallization of this material from hot methanol gave 1,3,6-tri-O-acetyl-4-O-(2,3,4,6-tetra-O-acetyl-β-D-galactopyranosyl)-2-azido-2-deoxy-β-D-glucopyranose (XXXII). The partial p.m.r. spectrum of compound XXXII in CDCl$_3$ gave, p.p.m. 5.51 (d, 1, $J_{1,2}$ 8.75 Hz, H-1), 3.57 (q, 1, $J_{2,3}$ 10.0 Hz, H-2).

EXAMPLE XI

Preparations of the 2-acetamido-1,3,4,6-tetra-O-acetyl-2-deoxy-α- and β-D-galactopyranoses (XXXIV and XXXV)

This example provides an efficient process, based on reduction by zinc, for the conversion of the mixture of anomeric 1,3,4,6-tetra-O-acetyl-2-azido-2-deoxy-D-galactoses, XXVII and XXVIII, obtained in Example VIII to an anomeric mixture of the 1,3,4,6-tetra-O-acetyl-2-acetamido-2-deoxy-galactopyranoses, XXIV and XXV, and how this mixture is useful for the preparation of D-galactosamine hydrochloride (XXXVII).

Glacial acetic acid (200 ml) and sodium acetate (8.2 g, 0.1 mole) were added to the α- and β-anomeric mixture of 3,4,6-tri-O-acetyl-2-azido-2-deoxy-α-D-galactopyranosyl nitrates (II and III) (32 g, 0.08 mole) prepared by the method of Example II and the mixture was stirred for one hour at 100°. Zinc metal (12.8 g, 0.2 mole) was then added to the solution cooled to 60° and stirred for 15 minutes. Acetic anhydride (17 ml) was added and the mixture heated on the steam bath (100°) for one hour and filtered. The solution was poured into 100 ml of water and stirred for one hour. Then 300 ml of water was added and the mixture extracted three times with dichloromethane (100 ml). The extracts were combined, filtered through dichloromethane-wetted paper and evaporated to a thick syrup which hardened to a crystalline mass on trituration with ether. The p.m.r. spectrum of this product was in agreement with that expected for a 4:1 mixture of the α- and β-anomers of 2-acetamido-1,3,4,6-tetra-O-acetyl-2-deoxy-D-galactopyranose.

Recrystallization from ether provided the pure α-anomer (XXXIV) in 55% yield; m.p. 177°–178°; $[\alpha]_D^{25}+99°$ (c 1, chloroform).

The mother liquors were combined to provide 14 g of a syrupy product which was found to be a near 1:1 anomeric mixture of the tetraacetates XXXIV and XXXV. The mixture was dissolved in 4 N aqueous hydrochloric acid (150 ml) and the solution heated at 100° for 7 hours. The solution was decolorized with activated charcoal and diluted with n-butanol (500 ml) prior to evaporation to a brownish syrup (10 g). The product was formed to be D-galactosamine hydrochloride XXXVII by comparison of its paper chromatographic mobility and its p.m.r. spectrum in D$_2$O to those of an authentic sample. Pure D-galactosamine hydrochloride was readily obtained by crystallization using ethanol-water-acetone as is described in the literature for the purification of this compound.

2-Acetamido-2-deoxy-D-galactose (XXXVI) can be prepared by simple N-acetylation of D-galactosamine hydrochloride, by methods well known to one skilled in the art, but is also available as an intermediate in the acid hydrolysis of compounds XXXIV and XXXV.

EXAMPLE XII

Preparation of 2-acetamido-1,3,4,6-tetra-O-acetyl-2-deoxy-α-D-galactopyranose (XXXIV)

Hydrogenation of 1,3,4,6-tetra-O-acetyl-2-azido-2-deoxy-α-D-galactopyranose (XXVII) (0.20 g, 0.536 mmole) dissolved in ethanol (3 ml) containing acetic anhydride (0.25 ml) and 5% palladium on charcoal (0.80 g) was complete in 1 hour at room temperature under 1 atmosphere of hydrogen. Filtration through diatomaceous earth and evaporation of the solvent gave a white foam (0.206 g). Examination by their layer chromatography on silica gel developed with 5:5:1 (v/v) benzene:ethyl acetate:ethanol showed the presence of two compounds which were readily separated by silica gel column chromatography (20×1 cm) eluted with the same solvent. This afforded 2-acetamido-1,3,4,6-tetra-O-acetyl-2-deoxy-α-D-galactopyranose (XXXIV) (0.10 g, 50% yield) which was recrystallized from ethyl ether, m.p. 177°–178°, $[\alpha]_D^{25}+99°$ (c 1, chloroform).

The p.m.r. data for compound XXXIV were in excellent agreement with those previously reported.

The second compound proved to be 2-(N-acetyl)acetamido-1,3,4,6-tetra-O-acetyl-2-deoxy-α-D-galactopyranose (0.068 g) by inspection of its p.m.r. spectrum and comparison of these data with those previously reported.

EXAMPLE XIII

Reduction of 1,3,4,6-tetra-O-acetyl-2-azido-2-deoxy-α-D-galactopyranose (XXVII) with hydrogen sulfide in the presence of triethylamine This example provides an alternate method for reducing the azido group to amine. Hydrogen sulfide was bubbled through a solution of compound XXVII (0.20 g, 0.53 mmole) and triethylamine (0.135 g, 1.34 mmole)

dissolved in dichloromethane (5 ml) at 0°. After 20 minutes, inspection of the reaction mixture by thin layer chromatography, developed with 10:10:1 (v/v) hexane:ethyl acetate:ethanol, showed no remaining starting material and one homogeneous spot of low $R_f$. A yellow precipitate was seen to appear upon standing. This suspension was evaporated to dryness and the residue was dissolved in pyridine (2 ml) and acetic anhydride (0.5 ml). After 15 hours, the reaction solution was diluted with dichloromethane (20 ml) and water (10 ml). The organic layer was separated, dried and evaporated to give a brown syrup (0.17 g), which had the same mobility on silica gel as 2-acetamido-1,3,4,6-tetra-O-acetyl-2-deoxy-α-D-galactopyranose (XXXIV). The p.m.r. spectrum of this syrup in CDCl$_3$ was identical to that of compound XXXIV.

EXAMPLE XIV

Preparation of D-galactosamine hydrochloride (XXVII) from the α- and β-3,4,6-tri-O-acetyl-2-azido-2-deoxy-D-galactopyranosyl nitrates II and III D-galactosamine hydrochloride (XXXVII) can be obtained directly from the anomeric mixture of 3,4,6-tri-O-acetyl-2-azido-2-deoxy galactopyranosyl nitrates, II and III, by hydrogenation to produce 3,4,6-tri-O-acetyl-D-galactosamine (XXXVIII) followed by acid hydrolysis, as is illustrated in this example.

A solution of the anomeric mixture of the 2-azido-2-deoxy nitrates II and III (1.0 g, 7.68 mmole) was hydrogenated in acetic acid (5 ml) containing 5% palladium on carbon (0.10 g) at one atmosphere and ambient temperature for 5 hours. After removal of the catalyst by filtration and evaporation of the solvent gave 3,4,6-tri-O-acetyl-D-galactosamine (XXXVIII) (0.85 g) as a foam. Treatment of this foam with 2 N aqueous hydrochloric acid (10 ml) at ambient temperature for two to three hours followed by dilution with n-butanol (5 ml) and evaporation gave D-galactosamine hydrochloride XXXVII (0.50 g) which was recrystallized from butanol-ethanol-water.

EXAMPLE XV

Preparation of D-galactosamine hydrochloride (XXXVII) from the α- and β-1,3,4,6-tetra-O-acetyl-2-azido-2-deoxy-D-galactopyranoses (XXVII) and (XXVIII)

D-galactosamine hydrochloride can also be produced in high yields from the anomeric mixture of the 2-azido-2-deoxy acetates XXVII and XVIII by acid hydrolysis followed by reduction. The process is demonstrated as follows.

A mixture of the anomeric compounds XXVII and XXVIII (1.0 g, 2.68 mmole) was dissolved in 2 N hydrochloric acid (10 ml) and stirred for two to three hours at room temperature. Dilution with n-butanol (5 ml) and evaporation of the solvent gave a white solid (0.510 g). Recrystallization of this solid from ethanol by evaporation gave pure 2-azido-2-deoxy-D-galactopyranose XL (0.40 g, 72% yield); m.p. 173°–175° (decomposition), $[\alpha]_D^{25}$ +53.7°→76.9° (c 0.98, water). Reduction of compound XL under acidic conditions gave D-galactosamine hydrochloride XXXVII.

One can also obtain 2-azido-2-deoxy-galactopyranose (XL) by similar treatment of N-(3,4,6-tri-O-acetyl-2-azido-2-deoxy-α-D-galactopyranosyl) acetamide (V).

EXAMPLE XVI

Preparation of 2-deoxy-D-lactosamine hydrochloride (XXXIX)

Example XVI describes the synthesis of D-lactosamine hydrochloride (XXXIX) from the 2-azido-2-deoxy lactosyl acetates, XXXI and XXXII.

An anomeric mixture of the 2-azido-2-deoxy-lactose acetate, compounds XXXI and XXXII, (5.0 g, 7.75 mmole) was dissolved in anhydrous methanol which was 5% in hydrogen chloride (20 ml) and stirred for two to three hours at room temperature. Dilution of this solution with n-butanol (10 ml) and evaporation of the solvent gave a light yellow syrup (1.40 g). Reduction of this compound with hydrogen in the presence of palladium and hydrochloric acid gave 2-deoxy-D-lactosamine hydrochloride (XXXIX).

Conversion of Azidonitrates to Azidohalides

The nitrate group, being strongly electronegative, serves as a good leaving group and, especially when at the anomeric center of sugar structures, is readily displaced by nucleophiles. Of special interest is the preparation, from the aforementioned 2-azido-2-deoxyglycosyl nitrates, of 2-azido-2-deoxyglycosyl halides since these latter substances can be used for the preparation of 2-azido-2-deoxyglycosides under conditions for glycosidation generally known in carbohydrate chemistry.

The displacement reaction, illustrated in Examples VIII through XIII, involves the treatment of the novel 2-azido-2-deoxy glycosyl nitrates with a halide salt to effect the displacement of the nitrate group by substitution by the halide. This reaction is well known to those skilled in the art and by virtue of the novel starting material leads to the formation of the novel 2-azido-2-deoxy glycosyl halides.

Similar to the nitrates, the α-glycosyl halides are more stable than their corresponding β-anomers. This will be evident in Examples XVII–XXI wherein the α-anomer is the predominant product. The β-glycosyl halides will anomerize to the more stable α-form in the presence of a large concentration of the halide ion. The rate of anomerization for the halides decreases in the order

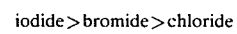

iodide > bromide > chloride

As will be demonstrated in Example XXII, the β-anomer can be produced in high yield under conditions of kinetic control. The 2-azido-2-deoxy glycosyl halides are useful in the preparation of 2-amino-2-deoxy glycosides. The α-glycosides, important building units in biological systems, can be obtained in good yield by route of the β-halides.

The preferred halide salts for the halogenation reaction are the tetraalkylammonium halides and the alkali metal halides, but the process is not limited to these.

The preferred solvent is acetonitrile but other aprotic, inert solvents, such as acetone, dimethylformamide and ethyl acetate, are suitable.

Broadly stated, a process is provided for producing a 2-azido-2-deoxy glycosyl halide which comprises reacting an acylated 2-azido-2-deoxy glycosyl nitrate with a halide salt in a suitable solvent.

More specifically, an anomeric mixture of the 3,4,6-tri-O-acetyl-2-azido-2-deoxy-D-galactopyranosyl nitrate, II and III, is reacted with tetraethylammonium chloride in acetonitrile to produce an anomeric mixture of 3,4,6-tri-O-acetyl-2-azido-2-deoxy-D-galactopyranosyl chloride.

In a preferred embodiment, the β-chloride is prepared in high yield by reacting an anomeric mixture of 3,4,6-tri-O-acetyl-2-azido-2-deoxy-D-galactopyranosyl nitrate, II and III, with anhydrous lithium iodide in acetonitrile to obtain 3,4,6-tri-O-acetyl-2-azido-2-deoxy-α-D-galactopyranosyl iodide (XXIV) as the predominant product. The product is immediately treated with a molar equivalent of tetraethylammonium chloride in acetonitrile. The mixture is cooled, and extraction affords 3,4,6-tri-O-acetyl-2-azido-2-deoxy-β-D-galactopyranosyl chloride (XXIII) in approximately 60% yield.

The 2-azido-2-deoxy glycosyl halides are useful in the preparation of 2-azido-2-deoxy glycosides under conditions for glycosidation generally known in carbohydrate chemistry as Koenings-Knorr conditions. These reactions will be discussed later.

EXAMPLE XVII

Preparation of 3,4,6-tri-O-acetyl-2-azido-2-deoxy-α-D-galactopyranosyl bromide (XX)

3,4,6-tri-O-acetyl-2-azido-2-deoxy-α-D-galactopyranosyl nitrate (II) (0.50 g, 1.34 mmole) was dissolved in anhydrous acetonitrile (4 ml) at room temperature containing lithium bromide (0.80 g, 9.38 mmole). After 40 minutes the solution was diluted with dichloromethane (25 ml) and washed with ice cold water (25 ml), dried over anhydrous sodium sulfate, and evaporated to give a clear syrup (0.40 g). The p.m.r. spectrum of this syrup had a doublet, J=4 Hz, at 6.51 p.p.m. which was assigned to the anomeric proton of 3,4,6-tri-O-acetyl-2-azido-2-deoxy-α-D-galactopyranosyl bromide (XX). This compound could not be crystallized.

EXAMPLE XVIII

Preparation of 3,4,6-tri-O-acetyl-2-azido-2-deoxy-α-D-galactopyranosyl chloride (XXII)

An about 1:2 mixture of the α- and β- anomers of 3,4,6-tri-O-acetyl-2-azido-2-deoxy-D-galactopyranosyl nitrate (0.377 g, 1.01 mmole) was dissolved in acetonitrile (6 ml) containing tetraethylammonium chloride (0.924 g, 5.05 mmole) and the solution was left at room temperature for 48 hours. The reaction mixture was diluted with dichloromethane (25 ml), washed with water (25 ml) and dried. Evaporation of the solvent in vacuo left a syrup (0.325 g) which showed doublets with spacings of 9.0 and 3.5 Hz at δ 5.15 and 6.20 p.p.m., respectively in the p.m.r. spectrum measured in CDCl$_3$. These signals are assigned to the β- (XXIII) and α- anomers (XXII) for 3,4,6-tri-O-acetyl-2-azido-2-deoxy-D-galactopyranosyl chloride, respectively. Judging from the relative intensities of the signals, the product consisted of a near 10:1 mixture of the α- and β-anomers, (XXII) and (XXIII) respectively.

EXAMPLE XIX

Preparation of 3,6-di-O-acetyl-4-O-(2,3,4,6-tetra-O-acetyl-β-D-galactopyranosyl)-2-azido-2-deoxy-α-D-glucopyranosyl chloride (XXV)

A mixture of the α- and β-anomers of 3,6-di-O-acetyl-4-O-acetyl-β-D-galactopyranosyl)-2-azido-2-deoxy-D-glucopyranosyl nitrate, (XIV) and (XV), (1.0 g, 1.5 mmoles) was treated with a solution of acetonitrile (20 ml) containing tetraethylammonium chloride (1.30 g, 7.8 mmoles) at ambient temperature for one hour. At that time the solution was diluted with dichloromethane (50 ml) and washed with water (2×50 ml). The organic layer was dried over anhydrous sodium sulfate, filtered, and evaporated to give a syrup which soon solidified. Recrystallization of this solid from ethyl acetate-ethyl ether gave pure 3,6-di-O-acetyl-4-O-(2,3,4,6-tetra-O-acetyl-β-D-galactopyranosyl)-2-azido-2-deoxy-α-D-glucopyranosyl chloride (XXV), m.p. 167°–168° C., $[\alpha]_D^{25} +59.3°$ (c 1, chloroform), in 66% yield.

The partial p.m.r. spectrum of compound XXV in CDCl$_3$ was, p.p.m. 6.08 (d, 1, $J_{1,2}$ 3.9 Hz, H-1), 3.74 (q, 1, $J_{2,3}$ 10 Hz, H-2).

EXAMPLE XX

Preparation of 3,6-di-O-acetyl-4-O-(2,3,4,6-tetra-O-acetyl-β-D-galactopyranosyl)-2-azido-2-deoxy-α-D-glucopyranosyl bromide (XXVI)

Treatment of a mixture of the α- and β- anomers of 3,6-di-O-acetyl-4-O-(2,3,4,6-tetra-O-acetyl-β-D-galactopyranosyl)-2-azido-2-deoxy-D-glucopyranosyl nitrate, (XIV) and (XV), (1.0 g, 1.5 mmoles) with a solution of acetonitrile (2 ml) containing lithium bromide (0.130 g, 1.5 mmoles) at ambient temperature for two to three hours, followed by workup of the product mixture by the method described in Example XII, gave a white foam (0.850 g) on evaporation. Crystallization of this material from ethyl acetate-ethyl ether gave pure 3,6-di-O-acetyl-4-O-acetyl-4-O-(2,3,4,6-tetra-O-acetyl-β-D-galactopyranosyl)-2-azido-2-deoxy-α-D-glucopyranosyl bromide (XXVI), m.p. 156°–157° C., $[\alpha]_D^{25} +87°$ (c 0.93, chloroform), in 41% yield.

The partial p.m.r. spectrum of compound (XXVI) in CDCl$_3$ was, p.p.m. 6.36 (d, 1, $J_{1,2}$ 3.9, H-1, 3.65 (q, 1, $J_{2,3}$ 10.2, H-2).

EXAMPLE XXI

Synthesis of 3,4,6-tri-O-acetyl-2-azido-2-deoxy-α-D-galactopyranosyl iodide (XXIV) in acetone 3,4,6-tri-O-acetyl-2-azido-2-deoxy-α-D-galactopyranosyl nitrate (II) (32.5 g, 0.087 mole) was treated with a solution of anhydrous sodium iodide (64.29 g, 0.43 mole) dissolved in acetone (259 ml) at room temperature for twenty minutes. At that time the reaction solution was treated by the method of Example XIX, to give a syrup (37.6 g). Examination of this syrup by p.m.r. showed it to be mainly 3,4,6-tri-O-acetyl-2-azido-2-deoxy-α-D-galactopyranosyl iodide (XXIV).

EXAMPLE XXII

Preparation of 3,4,6-tri-O-acetyl-2-azido-2-deoxy-β-D-galactopyranosyl chloride (XXIII)

Although the 3,4,6-tri-O-acetyl-2-azido-2-deoxy-α-D-galactopyranosyl bromides and chlorides can be prepared conveniently for later use, the corresponding α-iodide proved highly reactive and not readily amenable to purification. However, its high reactivity proved useful for the preparation of the β-chloride (XXIII) under conditions of kinetic control. That is, the α-iodide could be reacted with chloride ion to form the β-chloride (XXIII) at a rate much greater than the anomerization of the β-chloride to the α-chloride XXII. The preparation of the pure β-chloride is presented in the following example.

The mixture of 3,4,6-tri-O-acetyl-2-azido-2-deoxy-α- and β-D-galactopyranosyl nitrates (II and III) (0.781 g, 2.09 mmole) prepared as described in either Example I or Example II was added to a suspension of anhydrous lithium iodide (1.86 g, 14 mmole) in anhydrous acetonitrile (3 ml). This mixture was stirred in the dark at room temperature for 15-17 minutes and then poured into an ice cold 1% aqueous solution of sodium thiosulfate. A dichloromethane (10 ml) extract was dried over sodium sulfate, filtered and evaporated to give a white foam which discolored upon standing. The p.m.r. spectrum of this compound in CDCl₃ showed no remaining starting material and contained a doublet with J=4.0 Hz at 6.93 p.p.m. which was assigned to the anomeric proton of 3,4,6-tri-O-acetyl-2-azido-2-deoxy-α-D-galactopyranosyl iodide (XXIV). This α-D-iodide (XXIV) (2.09 mmole) was immediately treated with a molar equivalent of either tetraethylammonium chloride (0.344 g, 2.09 mmole) dissolved in anhydrous acetonitrile (2 ml) or lithium chloride (0.081 g, 2.0 mmole) at ambient temperature. After 1.5 minutes, the solution was poured into ice cold water (10 ml) and extracted with cold dichloromethane (10 ml). The organic solution was dried and evaporated to give a light yellow syrup which, on trituration with ethyl ether, afforded crystalline 3,4,6-tri-O-acetyl-2-azido-2-deoxy-β-D-galactopyranosyl chloride (XXIII) in 50-60% yield; m.p. 102°-104°, $[\alpha]_D^{25}$ −16.5 (c 1, chloroform).

The p.m.r. spectrum of compound XXIII in CDCl₃ showed, in part, p.p.m. 5.91 (q, 1, $J_{3,4}$ 3 Hz, H-4), 5.15 (d, 1, $J_{1,2}$ 9 Hz, H-1), 4.86 (q, 1, $J_{2,3}$ 10.5 Hz, H-3), 3.88 (q, 1, H-2).

Conversion of Glycosyl Halides to Glycosides

Glycosidation, under Koenigs-Knorr conditions, involves the treatment of a glycosyl halide with an alcohol, ROH, in the presence of a promoter. The promoter is commonly a salt or compound which contains a heavy atom, such as silver, lead or mercury, which can coordinate with the halogen atom so as to facilitate the cleavage of its bond with the anomeric carbon. The halogen is replaced by the alkoxy group, —OR, to produce the glycoside.

The novel α-glycosyl halides of 2-azido-2-deoxy-D-galactose, XX and XXII, prepared as shown in Examples XVII and XVIII and of 2-azido-2-deoxy-D-lactose, XXV and XXVI, as shown in Examples XIX and XX, can be used for the preparation of the novel 3,4,6-tri-O-acetyl-2-azido-2-deoxy-β-D-galactopyranosides (Examples XXIII, XXIV) and 2-azido-2-deoxy-β-D-lactosides (Example XXV), respectively, under conditions of the Koenigs-Knorr reaction.

Broadly stated, a process is provided which comprises reacting 3,4,6-tri-O-acetyl-2-azido-2-deoxy-β-D-galactopyranosyl chloride (XXIII) with an alcohol in the presence of a promoter to produce 3,4,6-tri-O-acetyl-2-azido-2-deoxy-α-D-galactopyranosides.

More specifically, 3,4,6-tri-O-acetyl-2-azido-2-deoxy-β-D-galactopyranosyl chloride (XXIII) is reacted with 8-methoxycarbonyloctyl-2-O-(2,3,4-tri-O-benzoyl-α-L-fucopyranosyl)-4,6-O-benzylidene-β-D-galactopyranoside (XLVII) in the presence of silver trifluoromethane sulfonate and silver carbonate in the solvent dichloromethane to produce 8-methoxycarbonyloctyl-3-O-(3,4,6-tri-O-acetyl-2-azido-2-deoxy-α-D-galactopyranosyl)-2-O-(2,3,4-tri-O-benzyl-α-L-fucopyranosyl)-4,6-O-benzylidene-β-D-galactopyranoside (XLVIII). This product was isolated and treated, by methods well known to persons skilled in the art, to accomplish the following: deblocking, that is conversion of the acetyl, benzyl, and benzylidene groups to hydroxyl groups, reduction of the azido group to an amine and acetylation of the amine. The final product of these steps is 8-methoxycarbonyloctyl-3-O-(2-acetamido-2-deoxy-α-D-galactopyranosyl)-2-O-(α-L-fucopyranosyl)-β-D-galactopyranoside, the terminal trisaccharide antigenic determinant for the human A blood group.

EXAMPLE XXIII

Preparation of t-butyl-3,4,6-tri-O-acetyl-2-azido-2-deoxy-β-D-galactopyranoside (XLI)

3,4,6-tri-O-acetyl-2-azido-2-deoxy-α-D-galactopyranosyl bromide (XX, 0.90 g, 2.28 mmole) prepared either by reaction of 1,3,4,6-tetra-O-acetyl-2-azido-2-deoxy-β-galactopyranose (XXVII) with hydrogen bromide in methylene chloride or by the method of Example XVII, was added to t-butyl alcohol (0.236 ml, 2.40 mmole) dissolved in methylene chloride (3 ml) which contained silver carbonate (1.8 g, 6.74 mmole) and 4 Å molecular sieves. After stirring for 1 hour at room temperature, the product was isolated in the conventional way to provide a syrup. P.m.r. examination of this syrup showed a doublet at 4.64 p.p.m. with $J_{1,2}$=9 Hz and a singlet at 1.31 p.p.m. which are assigned to the anomeric proton and aglycon, respectively of t-butyl-3,4,6-tri-O-acetyl-2-azido-2-deoxy-β-D-galactopyranoside (XLI), obtained in 75% yield.

EXAMPLE XXIV

Preparation of 8-methoxyoctylcarbonyl-3,4,6-tri-O-acetyl-2-acetamido-2-deoxy-β-D-galactopyranoside (XL)

A solution of 3,4,6-tri-O-acetyl-2-azido-2-deoxy-β-D-galactopyranosyl bromide (XXI) (1.0 g, 2.54 mmole) dissolved in dichloromethane (2 ml) was added to a mixture of 8-methoxycarbonyl octanol (0.565 g, 2.79 mmole), 4 Å molecular sieves, and silver carbonate (2.30 g, 8.37 mmole) in dichloromethane (5 ml) and stirred for 3 hours at room temperature. At that time the solution was filtered and the filtrate evaporated to give a syrup (1.30 g). This syrup was dissolved in acetic acid 10 ml containing acetic anhydride (10 ml) and zinc metal (1.17 g, 18 mmole) was added with stirring. After 20 minutes the solids were removed by filtration and the filtrate concentrated to approximately 2 or 3 ml. This was diluted with dichloromethane (25 ml) and washed with saturated aqueous sodium bicarbonate (20 ml) and water (10 ml). Drying of the organic solution and evaporation gave a syrup (1.0 g, 75% yield) which was shown by examination of its p.m.r. spectrum in CDCl₃ to be essentially pure 8-methoxyoctylcarbonyl-2-acetamido-3,4,6-tri-O-acetyl-2-deoxy-β-D-galactopyranoside (XLII). A partial p.m.r. of this compound in CDCl₃ gave; p.p.m. 6.40 (d, 1, $J_{NH,2}$ 8.2 Hz, NH), 4.70 (d, 1, $J_{1,2}$ 8.0 Hz, H-1). The large coupling constant of 8.0 Hz for H-1 confirmed the formation of the β-D-glycosyl linkage.

EXAMPLE XXV

Synthesis of t-butyl-3,6-di-O-acetyl-4-O-(2,3,4,6-tetra-O-acetyl-β-D-galactopyranosyl)-2-azido-2-deoxy-β-D-glucopyranoside (XLIII)

Treatment of the 2-azido-2-deoxy-lactosyl bromide XXVI (1.0 g, 1.46 mmoles) (prepared by the method of Example XXIII for two hours gave) after conventional work up, the compound XLIII (0.80 g, 80%).

Deacetylation and reduction of the azido group, followed by N-acetylation, of compound XLIII by the method of Example XI gave the corresponding 2-acetamido-2-deoxy-β-D-lactosyl glycoside (XLIV).

An outstanding feature of this invention is the provision of 3,4,6-tri-O-acetyl-2-azido-2-deoxy-β-D-galactopyranosyl chloride (XXIII) as a reagent for the preparation of 2-amino-2-deoxy-α-D-galactopyranosides as depicted in formula A.

In the following examples, compound XXIII is used to prepare a simple glycoside (Example XXVI), a disaccharide (Example XXVII) and the trisaccharide antigenic determinant for the human A blood group (Example XXVIII).

EXAMPLE XXVI

Synthesis of t-butyl-3,4,6-tri-O-acetyl-2-azido-2-deoxy-α-D-galactopyranoside (XLV)

A solution of freshly prepared 3,4,6-tri-O-acetyl-2-azido-2-deoxy-α-D-galactopyranosyl chloride (XXII, 0.160 g, 0.458 mmole) in dichloromethane (1 ml) was added dropwise to a mixture of silver trifluoromethanesulfonate (0.010 g, 0.039 mmole), silver carbonate (0.443 g, 1.61 mmole), 4 A molecular sieves (0.150 g), and t-butanol (55 μl, 0.583 mmole) in dichloromethane. This mixture was stirred for 2.5 hours in the dark and then filtered and the resulting filtrate evaporated to dryness to give a syrup (0.150 g). The p.m.r. spectrum of this material in CDCl$_3$ indicated the presence of about 60% α-t-butyl glycoside (XLV) by the presence of a singlet at 0.30 p.p.m. The anomeric proton was obscured by signals for H-4 and H-3 near 5.1 p.p.m.

EXAMPLE XXVII

Preparation of 8-Methoxycarbonyloctyl-3-O-(2-acetamido-2-deoxy-α-D-galactopyranosyl)-β-D-galactopyranoside (XLVII)

A solution of freshly prepared 3,4,6-tri-O-acetyl-2-azido-2-deoxy-β-D-galactopyranosyl chloride XXIII (0.335 g, 0.96 mmole) in dichloromethane (1 ml) was added to a mixture of silver trifluoromethanesulfonate (0.022 g, 0.085 mmole), silver carbonate (1.06 g, 3.85 mmole), 4 A molecular sieves (0.70 g) and 8-methanoxycarbonyloctyl-4,6-O-benzylidene-2-O-benzoyl-β-D-galactopyranoside XLV (0.250 g, 0.461 mmole) in dichloromethane (4 ml). After 4 hours at ambient temperature the mixture was filtered through diatomaceous earth which was washed with dichloromethane (10 ml). This solution was evaporated to give a syrup which was dissolved in a small amount of 1:1 (v/v) benzene:ethyl acetate and chromatographed on neutral aluminum oxide (15 g), in a column (10×2 cm), eluted with the same solvent, to afford a syrup (0.524 g). Crystallization of this syrup from ethyl acetate:pentane afforded crude 8-methoxycarbonyloctyl-3-O-(3,4,6-tri-O-acetyl-2-azido-2-deoxy-α-D-galactopyranosyl)-4,6-O-benzylidene-2-O-benzoyl-β-D-galactopyranoside (0.324 g) in 79% yield. Recrystallization gave the pure compound m.p. 175°–176°, $[\alpha]_D^{25}+119.7°$ (c 1, chloroform), i.r. (film) 2120 cm$^{-1}$ (—N$_3$).

The p.m.r. spectrum of this latter compound in CDCl$_3$ contained in part at 4.62 p.p.m., a doublet with $J_{1,2}=8.0$ Hz which was assigned to H-1. The signal for H-1' was obscured by signals for H-3' and H-4'. That the newly formed intersugar glycosidic linkage was α was shown by the presence of the signal in the $^{13}$C-spectrum of the compound in CDCl$_3$ at 95.4 p.p.m. which was assigned to C-1'. The signal assigned to C-1 was observed at 100.7 p.p.m. Hydrogenation followed by N-acetylation and removal of the acetyl and benzoyl blocking groups as described in Example XXVII for the preparation of compound L gave crystalline 8-methoxycarbonyloctyl-3-O-(2-acetamido-2-deoxy-α-D-galactopyranosyl)-β-D-galactopyranoside, (XLVII). Recrystallization from methanol-ethyl ether gave pure XLVIII; m.p. 214°–216°, $[\alpha]_D^{25}+126.3°$ (c 0.98, water).

EXAMPLE XXVIII

Preparation of 8-methoxycarbonyloctyl-3-O-(2-acetamido-2-deoxy-α-D-galactopyranosyl)-2-O-(α-L-fucopyranosyl)-β-D-galactopyranoside L In this example, the alcohol has a disaccharidic structure and the glycosidation product is treated to convert the acetyl, benzyl, and benzoyl groups to hydroxyl groups (deblocking) and to reduce the azido group to amine which is then acetylated. The method used to perform the above deblocking, reduction and acetylation reactions are well known to persons skilled in the art.

A solution of freshly prepared 3,4,6-tri-O-acetyl-2-azido-2-deoxy-β-D-galactopyranosyl chloride (XXIII) (0.588 g, 1.6 mmole), dissolved in dichloromethane (2 ml), was added to a solution of silver trifluoromethanesulfonate (0.035 g, 0.136 mmole), silver carbonate (1.70 g, 6.18 mmole), 4 A molecular sieves (1.12 g), and 8-methoxycarbonyloctyl-2-O-(2,3,4-tri-O-benzyl-α-L-fucopyranosyl)-4,6-O-benzylidene-β-D-galactopyranoside (XLVIII) (0.787 g, 0.9 mmole) in dichloromethane (5 ml). After 4 hours at ambient temperature the mixture was diluted with dichloromethane (10 ml) and filtered through diatomaceous silica and the filtrate was then evaporated to give a syrup (1.25 g). This syrup was chromatographed on a column (44×2 cm) of silica gel with 2:1 (v/v) benzene:ethyl acetate as the eluent, to afford pure 8-methoxycarbonyloctyl-3-O-(3,4,6-tri-O-acetyl-2-azido-2-deoxy-α-D-galactopyranosyl)-2-O-(2,3,4-tri-O-benzyl-α-L-fucopyranosyl)-4,6-O-benzylidene-β-D-galactopyranoside XLIX (0.780 g, 75% yield), $[\alpha]_D^{25}+15.5°$ (c 1, chloroform), i.r. (film) 2110 cm$^{-1}$ (—N$_3$).

The p.m.r. spectrum of compound XLIX in CDCl$_3$ had in part, 5.47 (d, 1, $J_{1'',2''}$ 3.4 Hz, H-1''), 5.32 (d, 1, $J_{1'}$, $_{2'}$ 3 Hz, H-1'). Its $^{13}$C-n.m.r. spectrum in CDCl$_3$ clearly showed the two α-glycosidic intersugar anomeric carbon atoms with signals at 97.9 p.p.m. and 94.0 p.p.m. for C-1' of the fucosyl unit and C-1'' of the 2-azido-2-deoxy galactosyl unit, respectively. The signal assigned to C-1 of the galactosyl unit occurred at 100.5 p.p.m.

Compound L (0.10 g, 0.085 mmole) was dissolved in ethyl acetate (2 ml) containing acetic anhydride (0.2 ml) and hydrogenated in the presence of 5% palladium on charcoal (0.06 g) at 100 p.s.i. and ambient temperature.

After 23 hours the solution was filtered and evaporated to give a foam. The infrared spectrum of this compound showed the absence of an azide group. This compound was deblocked or deacetylated with sodium methoxide in anhydrous methanol (5 ml) at ambient temperature for 15 hours. After deionization and filtration, evaporation of the solvent gave a foam (0.08 g). Hydrogenation of this material in ethanol (3 ml) in the presence of 5% palladium on charcoal (0.065 g) at ambient temperature and 100 p.s.i. for 40 hours followed by filtration and evaporation gave 8-methoxycarbonyloctyl-3-O-(2-acetamido-2-deoxy-α-D-galactopyranosyl)-2-O-(α-L-fucopyranosyl)-β-D-galactopyranoside (XLIX) (0.046 g, 78% yield) as a white solid.

The p.m.r. spectrum of compound L in $D_2O$ was consistent with the assigned structure and showed in part, p.p.m. 5.62 (d, 1, $J_{1'}$, $_{2'}$ 1 Hz, H'), 5.46 (d, 1, $J_{1''}$, $_{2''}$ 3.5 Hz, H-1"), 2.24 (s, 3, NAc). This compound is the trisaccharide antigenic determinant for the human A blood group.

EXAMPLE XXIX

Preparation of an immunoabsorbent (LII) specific for anti-A antibodies

The trisaccharide antigenic determinant (L) for the human A blood group can be used to prepare an artificial antigen by attachment to a soluble carrier molecule such as proteins, red blood cells, polypeptides and soluble aminated polysaccharides using known methods.

The glycoside L can also be used to prepare an immuno-absorbent specific for anti-A antibodies by attachment to an insoluble support such as aminated glass, aminated polyacrylamide, aminated polyvinyl, aminated agarose and other insoluble aminated polysaccharides. This process is demonstrated below.

8-Methoxycarbonyloctyl-3-O-(2-acetamido-2-deoxy-α-D-galactopyranosyl)-2-O-(α-L-fucopyranosyl)-β-D-galactopyranoside (L) (0.044 g, 0.063 mmole) was stirred with 85% hydrazine hydrate (2 ml) at room temperature for 90 minutes. Examination by thin layer chromatography of the reaction mixture, on silica gel developed with 7:1:2 (v/v) isopropanol: ammonium hydroxide:water, showed no remaining starting material. This solution was diluted with 50% aqueous ethanol (1 ml) and evaporated to dryness to give a white foam (0.044 g). The material was dissolved in water (2 ml) and dialyzed against five changes of distilled water in an ultrafiltration cell equipped with a membrane with a molecular weight cut-off of 500 and freeze-dried to give the corresponding hydrazide LI as a white solid (0.039 g).

The p.m.r. spectrum of compound L in $D_2O$ was consistent with the assigned structure and had in part, p.p.m. 5.58 (d, 1, J>1 hz, H-1'), 5.44 (d, 1, $J_{1''}$, $_{2''}$ 3.5 Hz, H-1"), 2.30 (s, 3, NAc).

The hydrazide LI (0.35 g, 0.05 mmole), was dissolved in dimethylformamide (0.7 ml) and cooled to −25°. A solution of dioxane (0.057 ml) which was 3.5 N in hydrochloric acid was added and this was followed by t-butyl nitrate (0.007 g, 0.069 mmole) dissolved in dimethylformamide (0.1 ml). This mixture was stirred for 30 minutes at −25° at which time sulfamic acid (0.0049 g, 0.052 mmole) was added. After 15 minutes, this solution was added dropwise to silylaminated glass beads (5.0 g) suspended in a buffer solution (25 ml) 0.08 M in $Na_2B_4O_7$ and 0.35 M in $KHCO_3$ at 0°. This suspension was tumbled slowly at 3°–5° for 26 hours at which time the support was filtered and washed with water (500 ml). The beads were then suspended in saturated sodium bicarbonate (30 ml) and 5% aqueous acetic anhydride (30 ml) was added and agitated for 15 minutes. The beads were then filtered and washed with water (500 ml) and suspended in phosphate buffered saline (pH 7) (25 ml) and subjected to reduced pressure for 15 minutes. Filtration and water washing (100 ml) gave the hydrated immunoabsorbent LIII (11.2 g). A phenol-sulfuric assay for total hexose on this immunoabsorbent before acetylation indicated a loading of 6 μmole of hapten per gram of support.

The immunoabsorbent LIII was found to selectively remove anti-A blood group antibodies from human sera. Thus, for example, treatment of 1 ml of a serum which effectively agglutinated human A blood cells with 200 mg of the immunoabsorbent LII removed these antibodies responsible for the agglutination within 20 minutes. The use of the immunoabsorbent in the form of a packed column was more efficient.

The embodiments of the invention in which an exclusive property or privilege is claimed are defined as follows:

1. A process which comprises reacting a protected glycal with ceric ammonium nitrate and an azide salt in a suitable solvent with stirring to form 2-azido-2-deoxy glycosyl nitrates.

2. The process of claim 1 wherein the protected glycal is an O-acylated derivative of the group consisting of D-galactal, D-glucal, D-xylal, D-arabinal, L-fucal, D-lactal and D-maltal;
the azide salt is one of the group consisting of sodium azide, lithium azide and potassium azide; and
the reaction temperature is maintained between −25° C. and 25° C.

3. The process of claim 2 wherein the acyl groups of the O-acylated glycal is chosen from the group consisting of acetyl, propionyl and benzoyl.

4. The process of claim 1 wherein the protected glycal is 3,4,6-tri-O-acetyl-D-galactal.

5. The process of claim 2 wherein the solvent is acetonitrile;
the reaction is maintained for a time sufficient to consume substantially all of the protected glycal; and
the reaction is conducted in an inert atmosphere.

6. O-acylated-2-azido-2-deoxyglycosyl nitrates.

7. A mixture of the α- and β-anomers of 3,4,6-tri-O-acetyl-2-azido-2-deoxy-D-galactopyranosyl nitrate.

8. A mixture of the α- and β-anomers of 3,4,6-tri-O-acetyl-2-azido-2-deoxy-D-glucopyranosyl nitrate and of 3,4,6-tri-O-acetyl-2-azido-2-deoxy-D- mannopyranosyl nitrate.

9. A mixture of the α- and β-anomers of 3,6-di-O-acetyl-4-O-(2,3,4,6-tetra-O-acetyl- β-D-galactopyranosyl)-2-azido-2-deoxy-D-glycopyranosyl nitrate.

10. The process which comprises reacting an anomeric mixture of 3,4,6-tri-O-acetyl-2-azido-2-deoxy-D-galactopyranosyl nitrate with sodium acetate in acetic acid to form the 1,3,4,6-tetra-O-acetyl-2-azido-2-deoxy-D-galactopyranosyl acetates, isolating said product, and hydrolyzing said isolated product in an aqueous acid to provide 2-azido-2-deoxy-D-galactose.

11. A process which comprises:
reacting an acylated glycal with ceric ammonium nitrate and an azide salt in a suitable solvent with stirring to form acylated 2-azido-2-deoxy glycosyl nitrate; and reacting the acylated 2-azido-2-deoxy glycosyl nitrate with a halide salt in a suitable solvent to form 2-azido-2-deoxy glycosyl halide.

12. The process which comprises reacting an acylated 2-azido-2-deoxy glycosyl nitrate with a halide salt in a suitable solvent to form the acylated 2-azido-2-deoxy glycosyl halide.

13. The process of claim 12 wherein:
the halide salt is selected from the group consisting of the alkali metal halides and the tetraalkylammonium halides; and
the solvent is selected from the group consisting of acetonitrile and acetone.

14. The process of claim 13 wherein said glycosyl nitrate is 3,4,6-tri-O-acetyl-2-azido-2-deoxy-D-galactopyranosyl nitrate.

15. The process of claim 13 wherein said glycosyl nitrate is 3,6-di-O-acetyl-4-O-(2,3,4,6-tetra-O-acetyl-β-D-galactopyranosyl)-2-azido-2-deoxy-D-glucopyranosyl nitrate.

16. The process which comprises reacting an acylated-2-azido-2-deoxy glycosyl nitrate with an iodide salt in a suitable solvent to form the acylated-2-azido-2-deoxy-α-glycosyl iodide, and reacting said α-glycosyl iodide with a chloride salt in a suitable solvent to produce the acylated-2-azido-2-deoxy-β-glycosyl chloride.

17. The process of claim 16 wherein the glycosyl nitrate is 3,4,6-tri-O-acetyl-2-azido-2-deoxy-D-galactopyranosyl nitrate.

18. 3,4,6-tri-O-acyl-2-azido-2-deoxy-β-D-galactopyranosyl halide.

19. 3,4,6-tri-O-acyl-2-azido-2-deoxy-β-D-galactopyranosyl chloride.

20. 3,6-di-O-acyl-4-O-(2,3,4,6-tetra-O-acyl-β-D-galactopyranosyl)-2-azido-2-deoxy-α-D-glucopyranosyl halide.

21. 3,4,6-tri-O-acetyl-2-azido-2-deoxy-α-D-galactopyranosides.

22. The product having the structure

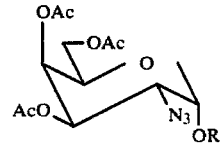

where $R=(CH_2)nCO_2R'$, $n=3-9$ and $R'$ is an alkyl or aryl group.

* * * * *

UNITED STATES PATENT AND TRADEMARK OFFICE
CERTIFICATE OF CORRECTION

PATENT NO. : 4,195,174
DATED : March 25, 1980
INVENTOR(S) : Raymond U. Lemieux et al.

It is certified that error appears in the above—identified patent and that said Letters Patent is hereby corrected as shown below:

Column 24, Claim 9, line 3, "D-glycopyranosyl" should read -- D-glucopyranosyl --.

Signed and Sealed this

Twenty-fourth Day of June 1980

[SEAL]

Attest:

SIDNEY A. DIAMOND

Attesting Officer

Commissioner of Patents and Trademarks